US012773219B2

(12) United States Patent
Kawamura et al.

(10) Patent No.: US 12,773,219 B2
(45) Date of Patent: Oct. 27, 2026

(54) HEMOSTATIC DEVICE

(71) Applicant: TERUMO KABUSHIKI KAISHA, Shibuya-ku (JP)

(72) Inventors: Tomoya Kawamura, Odawara (JP); Tatsuya Ouchi, Fujinomiya (JP); Koki Yamashita, Fuji (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 18/809,999

(22) Filed: Aug. 20, 2024

(65) Prior Publication Data

US 2024/0407790 A1 Dec. 12, 2024

Related U.S. Application Data

(63) Continuation of application No. PCT/JP2023/006127, filed on Feb. 21, 2023.

(30) Foreign Application Priority Data

Feb. 22, 2022 (JP) ................................ 2022-025345

(51) Int. Cl.
*A61B 17/135* (2006.01)
*A61B 17/12* (2006.01)

(52) U.S. Cl.
CPC .. *A61B 17/135* (2013.01); *A61B 2017/12004* (2013.01)

(58) Field of Classification Search
CPC .............. A61B 17/135; A61B 17/1325; A61B 17/12004
See application file for complete search history.

(56) References Cited

U.S. PATENT DOCUMENTS 5,464,420 A * 11/1995 Hori .................. A61B 17/1325 606/202
10,524,802 B2 1/2020 Kimura et al.
(Continued)

FOREIGN PATENT DOCUMENTS

| | | | |
|---|---|---|---|
| EP | 0554602 | A1 | 8/1993 |
| JP | H05277125 | A | 10/1993 |
| JP | 2021502220 | A | 1/2021 |

OTHER PUBLICATIONS

International Search Report (PCT/ISA/210) with translation and Written Opinion (PCT/ISA/237) mailed on Apr. 4, 2023, by the Japan Patent Office as the International Searching Authority for International Application No. PCT/JP2023/006127. (10 pages).
(Continued)

*Primary Examiner* — Brigid K Byrd
(74) *Attorney, Agent, or Firm* — BUCHANAN INGERSOLL & ROONEY PC

(57) ABSTRACT

A hemostatic device capable of appropriately aligning an inflatable portion in a deflated state with a puncture site, even in a case where inflating and deflating of the inflatable portion have been repeated, includes a cover member configured to cover a first puncture site, and a pressing member connected to the cover member and configured to compress the first puncture site. The pressing member includes an inflatable portion configured to be able to inflate and deflate by injection of a fluid, and an injection portion configured to be able to inject the fluid into the inflatable portion. The inflatable portion includes a bottom surface portion, a column portion rising from the bottom surface portion, and a curved surface portion forming an upper surface of the column portion in an inflated state. A thickness of the curved surface portion is formed to be thinner than a thickness of the column portion.

16 Claims, 19 Drawing Sheets

(56) References Cited

U.S. PATENT DOCUMENTS

| | | | | |
|---|---|---|---|---|
| 11,284,905 | B2 | 3/2022 | Kiemeneij et al. | |
| 2015/0327870 | A1* | 11/2015 | Fortson | A61B 17/0057 606/202 |
| 2018/0008283 | A1 | 1/2018 | Hazama et al. | |
| 2018/0199947 | A1 | 7/2018 | Benz et al. | |
| 2019/0133602 | A1 | 5/2019 | Kiemeneij et al. | |
| 2022/0370080 | A1 | 11/2022 | Kiemeneij et al. | |
| 2024/0423772 | A1* | 12/2024 | Forsell | A61N 1/36007 |

OTHER PUBLICATIONS

Extended European Search Report issued on Oct. 24, 2025, in corresponding European Patent Application No. 23759952.7. (10 pages).

Examination report under sections 12 & 13 of the Patents Act issued on Jun. 11, 2026, by the Indian Patent Office in Indian Patent Application No. 202417059283. (6 pages).

Notice of Reasons for Refusal issued on Sep. 1, 2026, by the Japanese Patent Office in corresponding Japanese Patent Application No. 2024-503156 and an English translation. (10 pages).

* cited by examiner

HEMOSTATIC DEVICE

CROSS-REFERENCES TO RELATED APPLICATIONS

This application is a continuation of International Patent Application No. PCT/JP2023/006127 filed on Feb. 21, 2023, which claims priority to Japanese Patent Application No. 2022-025345 filed on Feb. 22, 2022, the entire content of both of which is incorporated herein by reference.

TECHNOLOGICAL FIELD

The present invention generally relates to a hemostatic device.

BACKGROUND DISCUSSION

One known catheter procedure is a procedure in which various medical elongated bodies are introduced into a blood vessel through a puncture site formed by puncturing a blood vessel of the limb such as the arm or the hand of a patient to perform a procedure or a therapy on a lesion site. For example, Japanese Patent Application Publication No. 2021-502220 (JP 2021-502220 A discloses a hemostatic device for stopping bleeding at a puncture site formed to enable access to a blood vessel (including a distal radial artery) running in the hand.

The hemostatic device disclosed in the above-noted Japanese patent application publication includes a pressing member that applies a compressive force to a puncture site formed on the hand of a patient, and a band body for securing the pressing member to the hand of the patient. The pressing member includes an inflatable portion (bladder) that inflates as a fluid such as gas is injected and deflates as the fluid is discharged.

SUMMARY

When an operator such as a doctor (hereinafter, referred to as an "operator") performs hemostatic compression on a puncture site using the hemostatic device described above, the operator aligns portion (for example, a maximum inflatable portion) on an outer surface side of an inflatable portion with the puncture site so as to face the body surface of the patient. After confirming a state in which the inflatable portion is disposed at the puncture site by visual observation, or the like, the operator inflates the inflatable portion to apply a compressive force to the puncture site. In this event, in a case where the inflatable portion in the inflated state does not appropriately apply the compressive force to the puncture site due to an influence of the arrangement of the inflatable portion, or the like, the operator deflates the inflatable portion once and resolves the issue that caused the inflatable portion to not appropriately apply the compressive force to the puncture site. The operator aligns the inflatable portion with the puncture site again in a state where the inflatable portion is deflated.

When the inflatable portion is aligned with the puncture site again as described above, in a case where the inflatable portion has restorability such that the inflatable portion deforms to substantially the same shape as an initial shape before inflating (deflated shape before hemostatic compression using the inflatable portion is started, hereinafter simply referred to as an "initial shape"), when the inflatable portion deflates, the operator can easily align the inflatable portion with the puncture site in a similar manner to a case where the inflatable portion is aligned with the puncture site before the operator performs operation of inflating and deflating the inflatable portion.

However, the hemostatic device disclosed in the above-noted Japanese patent application publication does not assume that the inflatable portion is aligned with the puncture site again after operation of inflating and deflating the inflatable portion is performed as described above. Thus, the inflatable portion of the hemostatic device does not have sufficient restorability to an initial shape, and when the inflatable portion is disposed again at the puncture site, it becomes difficult for the operator to appropriately dispose a portion of the inflatable portion at the puncture site. Thus, in order to align the portion of the inflatable portion with the puncture site, the operator manually deforms the inflatable portion to a shape close to the initial shape by pressing an outer surface (liquid contact portion) of the inflatable portion to be disposed at the puncture site with the fingers while deflating the inflatable portion. The operator aligns the inflatable portion with the puncture site again after deflating the inflatable portion while touching the inflatable portion with the fingers. However, if the fingers touch the inflatable portion, there is a high possibility that blood flowing from the puncture site may unnecessarily adhere to the outer surface of the inflatable portion or contamination may occur at the puncture site.

The new hemostatic device disclosed here is capable of appropriately aligning an inflatable portion in a deflated state with a puncture site even in a case where inflating and deflating of the inflatable portion are repeated.

A hemostatic device according to one aspect includes: a cover member configured to cover a puncture site on a patient; and a pressing member connected to the cover member and configured to compress the puncture site. The pressing member includes an inflatable portion configured to be inflated by injection of a fluid into an interior of the inflatable portion and to be deflated, and an injection portion configured to inject the fluid into the interior of the inflatable portion. The inflatable portion includes a bottom surface portion, a column portion rising from the bottom surface portion, and a curved surface portion forming an upper surface of the column portion in an inflated state, and a thickness of the curved surface portion is thinner than a thickness of the column portion.

In the hemostatic device, the thickness of the column portion rising from the bottom surface portion of the inflatable portion is larger than the thickness of the curved surface portion forming the upper surface of the column portion. Thus, in the hemostatic device, when the inflatable portion inflates, the curved surface portion forming the upper surface of the column portion starts inflating earlier than the column portion. In addition, in the hemostatic device, when the inflatable portion deflates, the curved surface portion located at a position farther away from the bottom surface portion than the column portion starts deflating earlier than the column portion. As described above, in the hemostatic device, a starting point of deformation at the time of inflating and deflating is determined such that the curved surface portion starts inflating earlier than the column portion when the inflatable portion inflates and the curved surface portion starts deflating earlier than the column portion when the inflatable portion deflates. Thus, when the inflatable portion in the inflated state deflates, the inflatable portion has high restorability such that the inflatable portion deforms to substantially the same shape as the initial shape. Thereby, in the hemostatic device, an arbitrary portion of the inflatable portion can be easily aligned with the puncture site, for example, when the inflatable portion is aligned with the puncture site again after the inflatable portion disposed at the puncture site in the inflated state is deflated. This eliminates the need for the operator to perform operation such as pressing the outer surface of the inflatable portion with the fingers when deflating the inflatable portion in order to change arrangement of the inflatable portion with respect to the puncture site. Thus, in the hemostatic device, when the inflatable portion is aligned with the puncture site again, it is possible to prevent blood flowing from the puncture site from unnecessarily adhering to the outer surface of the inflatable portion or contamination from occurring at the puncture site.

Another aspect involves a hemostatic device comprising a cover member configured to cover a puncture site on a patient and a pressing member connected to the cover member and configured to compress the puncture site. The pressing member comprises an inflatable portion configured to be inflated to an inflated state by introducing a fluid into an interior of the inflatable portion and to be deflated and an injection portion in communication with the interior of the inflatable portion and configured to inject the fluid into the interior of the inflatable portion. The inflatable portion includes a bottom surface portion, a column portion extending away from the bottom surface portion, and a curved surface portion forming an upper surface of the column portion in the inflated state of the inflatable portion. The thickness of the curved surface portion is thinner than the thickness of the column portion, and the curved surface portion includes a top surface portion having a top portion that, in the inflated state of the inflation portion, is at a position farthest from the bottom surface portion side. The curved surface portion also includes an inclined portion that is located around the top surface portion and is connected to the column portion, and the inclined portion includes a thinned portion that surrounds the top surface portion and has a thickness less than a thickness of the top surface portion.

According to another aspect, a hemostatic device for applying compression to a puncture site of a patient comprises: a cover member configured to be positioned in overlying relation to the puncture site on the patient; and a pressing member connected to the cover member to apply the compression to the puncture site when the cover member is positioned in overlying relation to the puncture site on the patient, the cover member being positioned in overlying relation to the pressing member. The pressing member comprises an inflatable portion configured to be inflated to an inflated state by introducing a fluid into an interior of the inflatable portion and to be deflated, and the pressing member also comprises an injection portion in communication with the interior of the inflatable portion and configured to inject the fluid into the interior of the inflatable portion. The inflatable portion includes a bottom surface portion, a column portion and a curved surface portion. The column portion is fixed directly to the bottom surface portion and extends away from the bottom surface portion when the inflatable portion is in the inflated state. The column portion that extends away from the bottom surface portion when the inflatable portion is in the inflated state includes a part that is positioned closest to the bottom surface portion and an end opposite the part that is closest to the bottom surface portion. The curved surface portion extends from the end of the column portion to a part of the inflatable portion that contacts the patient when the compression is applied to the puncture site, and the curved surface portion has an outer surface, with at least a part of the outer surface of the curved surface portion being curved and having a thickness. The thickness of at least the part of the curved surface portion that is curved is less than the thickness of the part of the column portion that is positioned closest to the bottom surface portion.

DETAILED DESCRIPTION

Hereinafter, an embodiment of the hemostatic device disclosed here as an example of the new hemostatic device will be described with reference to the accompanying drawings. The following description does not limit the technical scope or the significance of each term disclosed in the claims. Furthermore, dimensional ratios of the drawings are exaggerated for illustration purpose and may differ from actual ratios. A range "X to Y" indicated in the present specification means "X or more and Y or less".

FIGS. 1 to 22 are views for explaining a hemostatic device 10 according to an embodiment. FIGS. 23 to 27 are views for explaining use examples of the hemostatic device 10 according to the embodiment.

Figure 23:
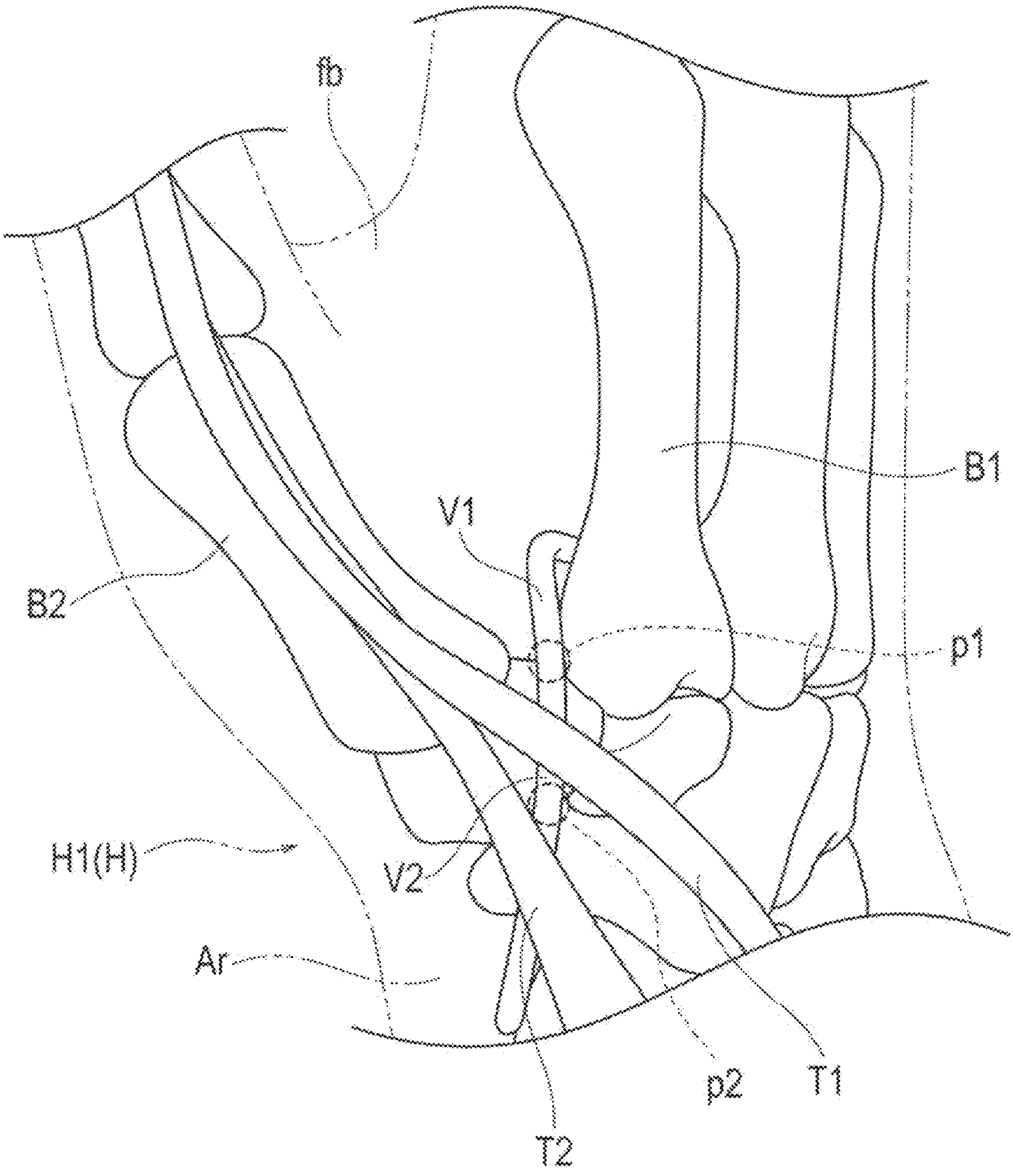
FIG. 23 is a view illustrating the hand (right hand) of a patient for which the hemostatic device is to be used.
Figure 26:
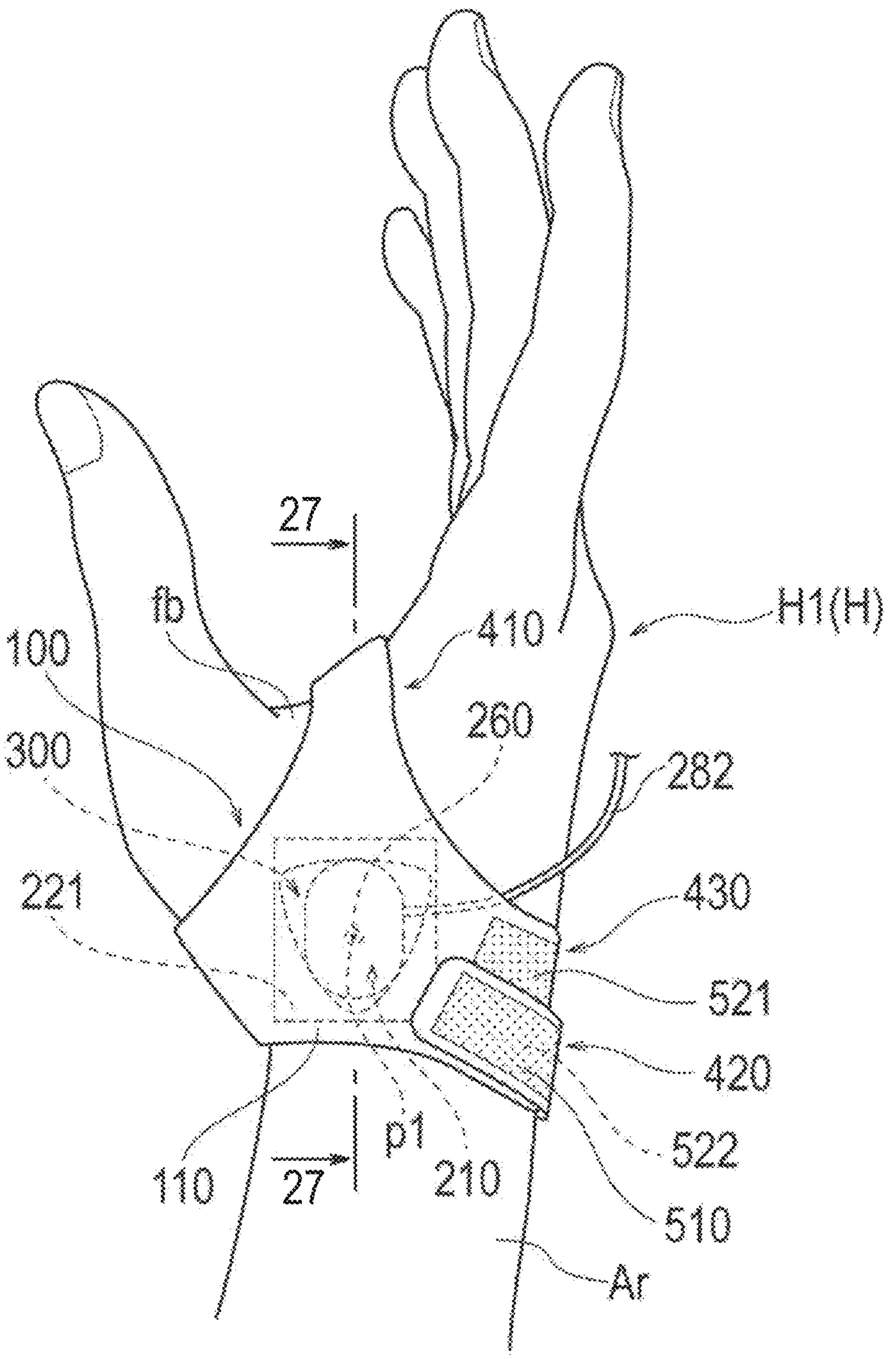
FIG. 26 is a view schematically illustrating a use example of the hemostatic device.
Figure 27:
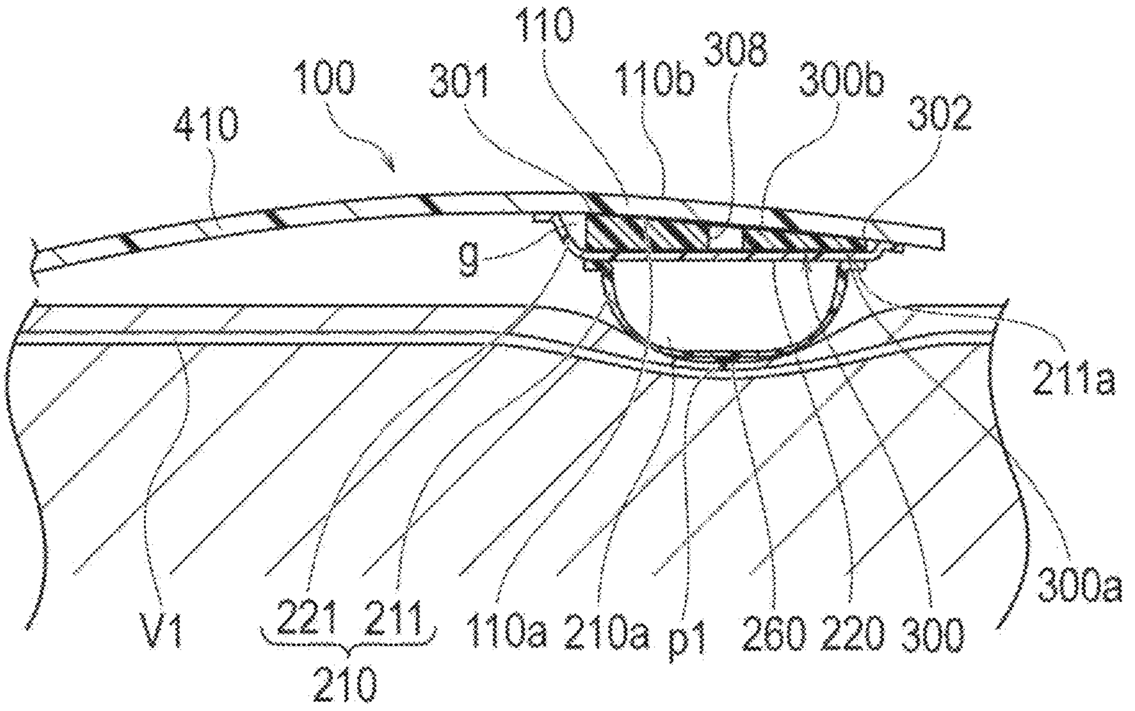
FIG. 27 is a partial cross-sectional view taken along the section line 27-27 in FIG. 26.

For example, as illustrated in FIGS. 23, 26, and 27, the hemostatic device 10 can be used to stop bleeding at a first puncture site p1 when a sheath tube 610 of an introducer 600 indwelled at the first puncture site p1 formed in the hand H located on a distal side (fingertip side) of the forearm Ar of a patient is removed.

A specific position of the puncture site where bleeding is to be stopped by the hemostatic device 10 is not particularly limited, but the first puncture site p1 and a second puncture site p2 are described as examples in the present specification.

As illustrated in FIGS. 23, 26, and 27, the first puncture site p1 is a puncture site formed in the distal radial artery (hereinafter, also referred to as a "blood vessel V1") located on the distal side of the snuff box of the palmar artery running on the dorsal side of the right hand H1 located on the distal side of the forearm Ar of the patient. In addition, the first puncture site p1 is located between the metacarpal B1 of the index finger and the metacarpal B2 of the thumb and is located at a predetermined position avoiding the metacarpal B1 of the index finger and the metacarpal B2 of the thumb. The snuff box is a cavity of the hand located near the radius when the patient spreads the thumb of the hand H.

As illustrated in FIG. 23, the second puncture site p2 is a puncture site formed in the artery V2 located in the snuff box of the palmar artery running on the dorsal side of the right hand H1. The second puncture site p2 is located on the forearm Ar side (proximal side) of the patient with respect to the first puncture site p1 and is located between the extensor pollicis longus tendon T1 and the extensor pollicis brevis tendon T2 located on the dorsal side of the right hand H1 of the patient. In addition, the second puncture site p2 is located at a predetermined position avoiding the position of the metacarpal B1 of the index finger and the position of the metacarpal B2 of the thumb.

The hemostatic device 10 can also be applied to hemostasis of a puncture site formed at a position on the left hand of the patient, corresponding to the first puncture site p1 on the right hand H1 of the patient, or a puncture site formed at a position on the left hand of the patient, corresponding to the second puncture site p2 on the right hand H1 of the patient.

Hereinafter, the hemostatic device 10 will be described in detail.

<Hemostatic Device>

As illustrated in FIGS. 1, 2, 26, and 27, the hemostatic device 10 includes a cover member 100 configured to cover the first puncture site p1 and a pressing member 200 connected to the cover member 100 and configured to compress the first puncture site p1.

<Pressing Member>

As illustrated in FIGS. 1, 2, 6, and 27, the pressing member 200 includes an inflatable portion 210 configured to be able to inflate and deflate by injection of a fluid, and an injection portion 270 configured to be able to inject a fluid into the inflatable portion 210.

<Inflatable Portion>

Figure 5:
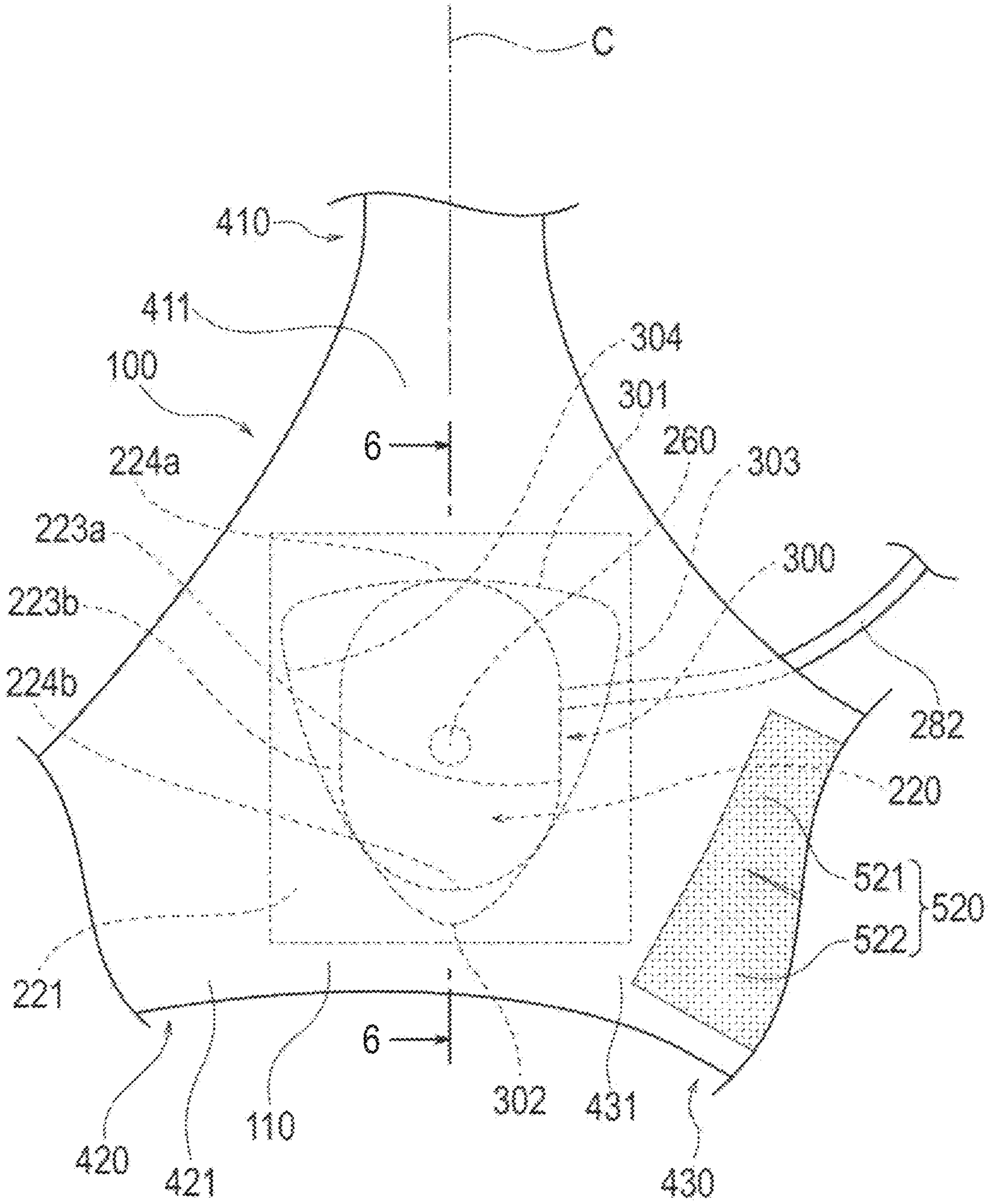
FIG. 5 is an enlarged view of part of the hemostatic device seen from the outer surface side of the cover member.
Figure 6:
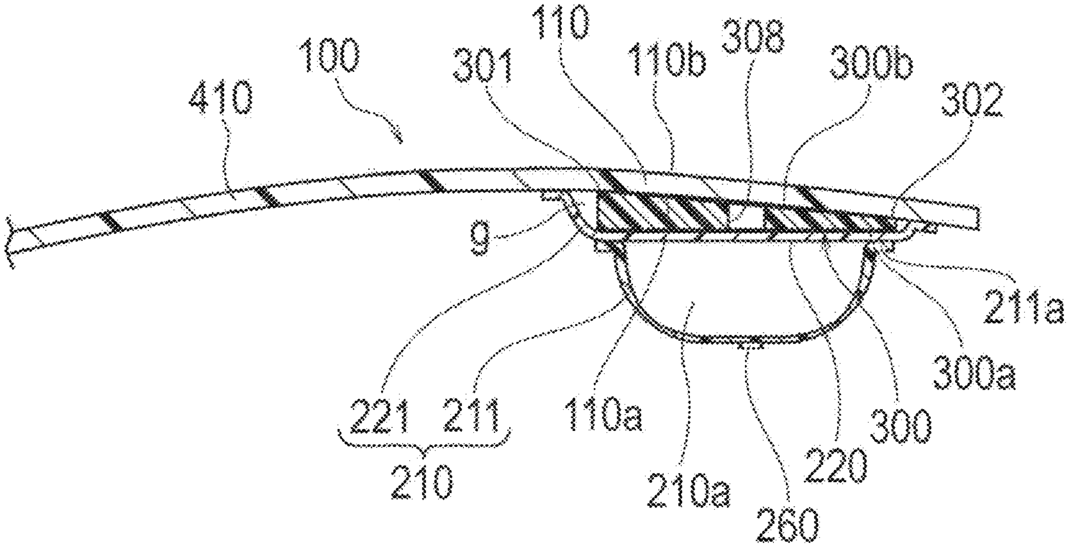
FIG. 6 is a partial cross-sectional view of the hemostatic device taken along the section line 6-6 in FIG. 5, and is a view illustrating a state when an inflatable portion is inflated.

FIG. 6 illustrates a partial cross-sectional view of the hemostatic device 10 along the section line 6-6 in FIG. 5. In addition, FIG. 6 illustrates a cross-sectional view of the inflatable portion 210 in an inflated state.

Figure 10:
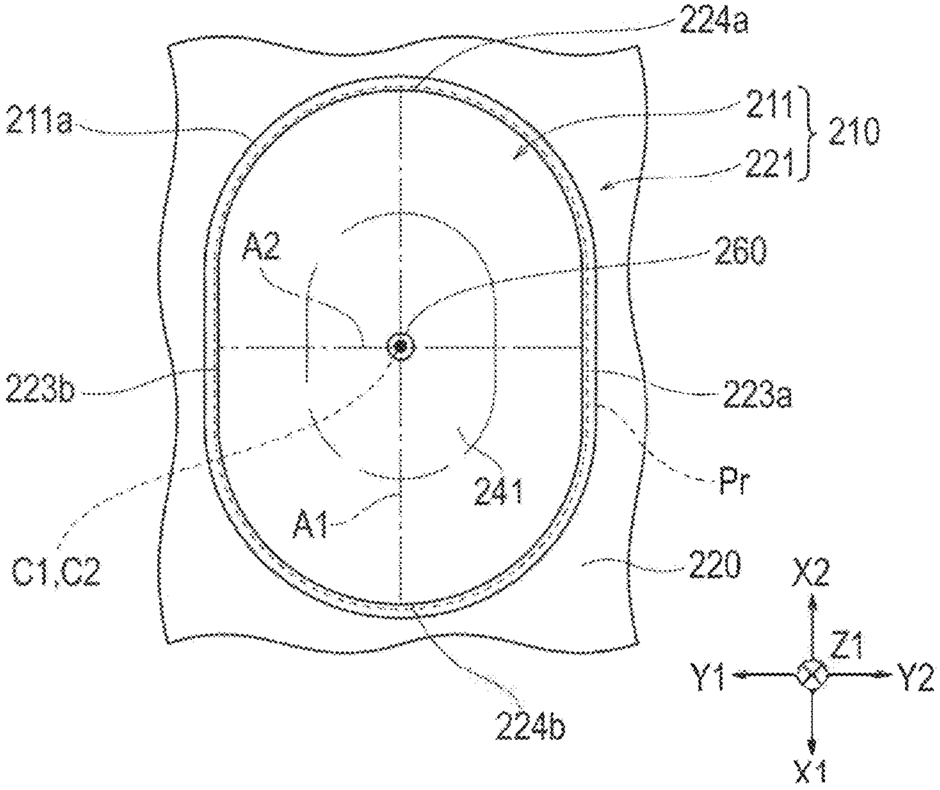
FIG. 10 is a plan view of the inflatable portion in an inflated state.
Figure 11:
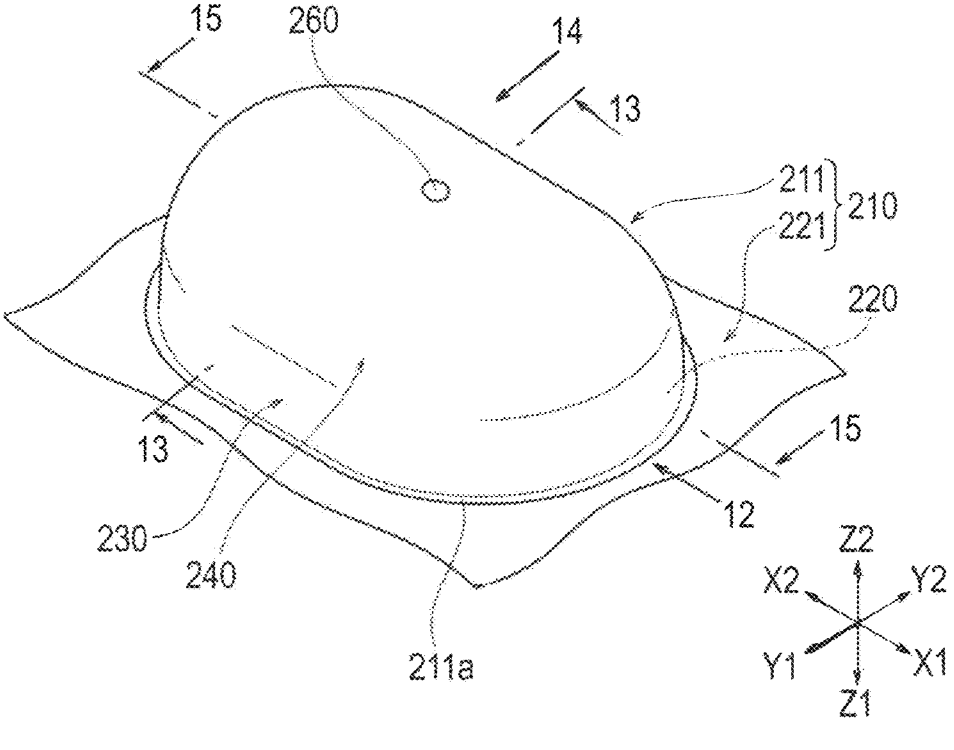
FIG. 11 is a perspective view of the inflatable portion in the inflated state.
Figure 12:
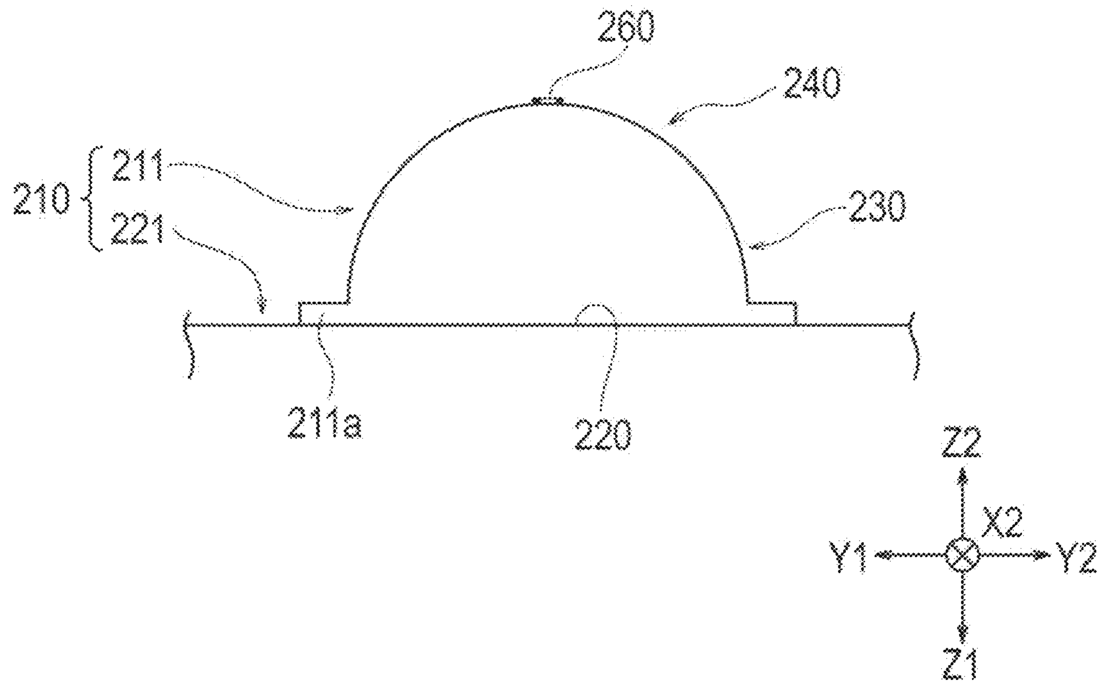
FIG. 12 is a front view of the inflatable portion seen from a direction of an arrow 12 in FIG. 11.
Figure 13:
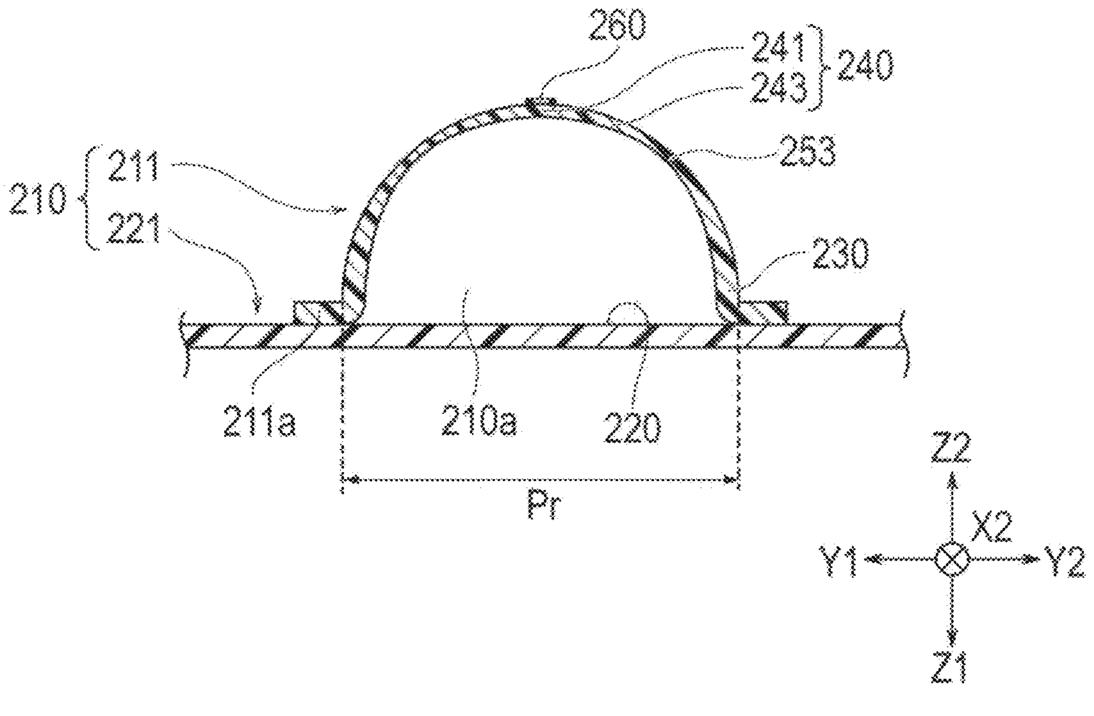
FIG. 13 is a cross-sectional view of the inflatable portion taken along the section line 13-13 in FIG. 11.
Figure 14:
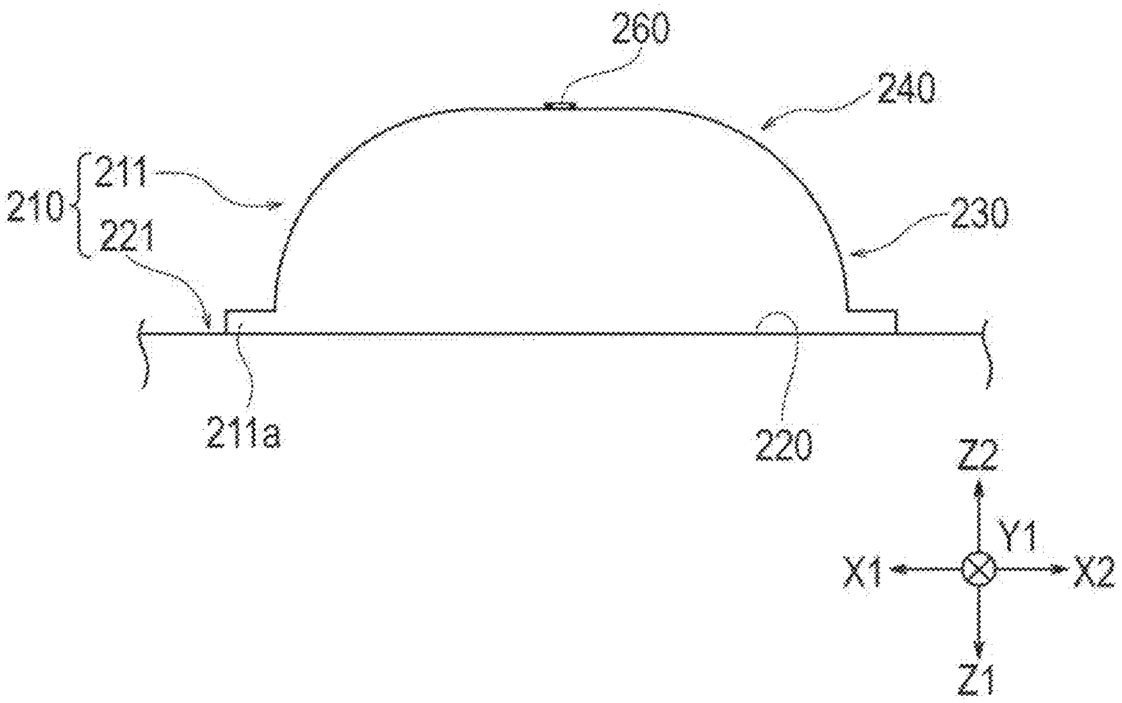
FIG. 14 is a side view of the inflatable portion seen from a direction of an arrow 14 in FIG. 11.
Figure 15:
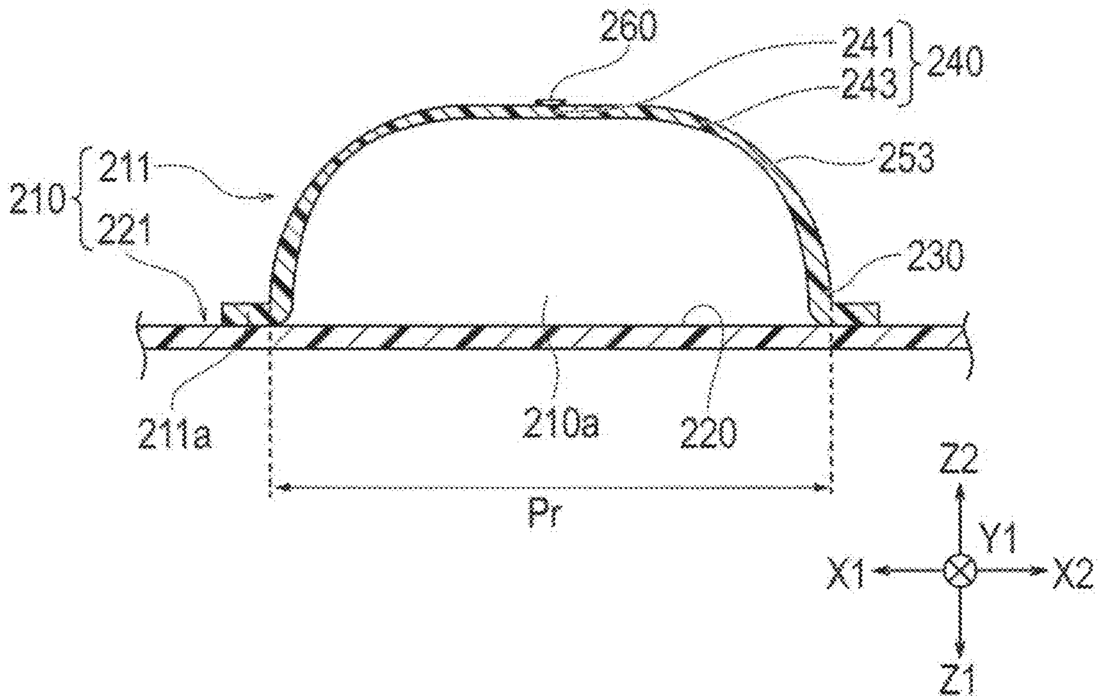
FIG. 15 is a cross-sectional view of the inflatable portion taken along the section line 15-15 in FIG. 11.
Figure 16:
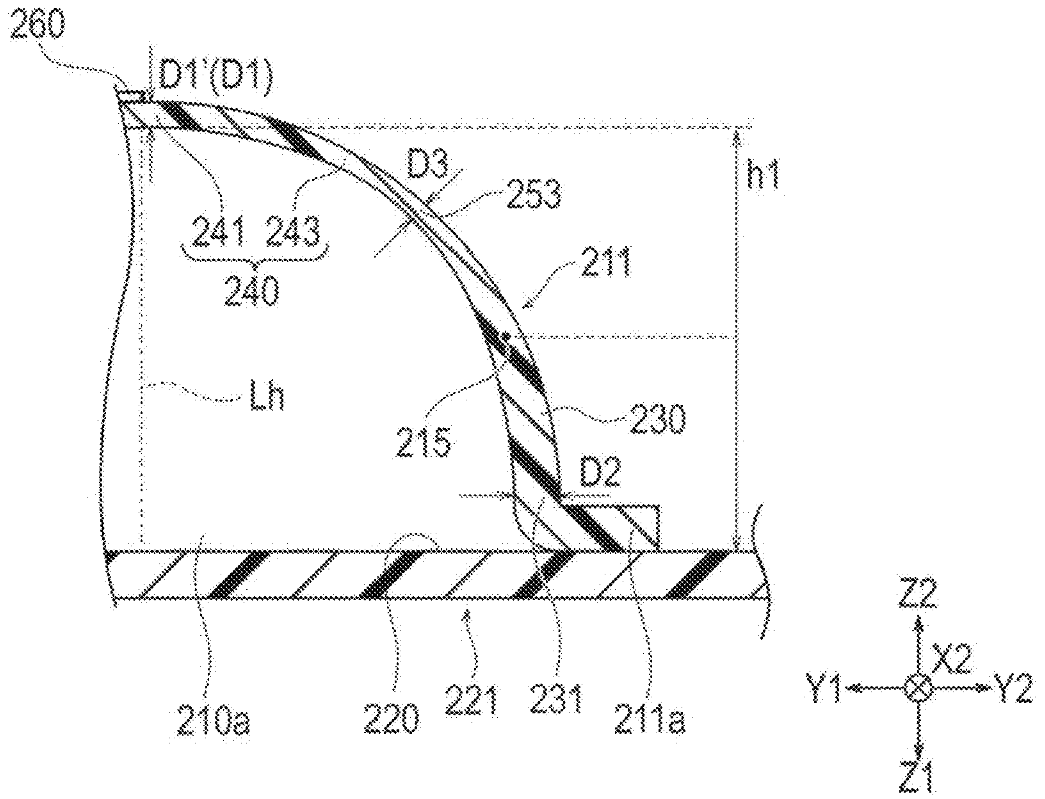
FIG. 16 is an enlarged view of part of the cross-sectional view illustrated in FIG. 13.
Figure 17:
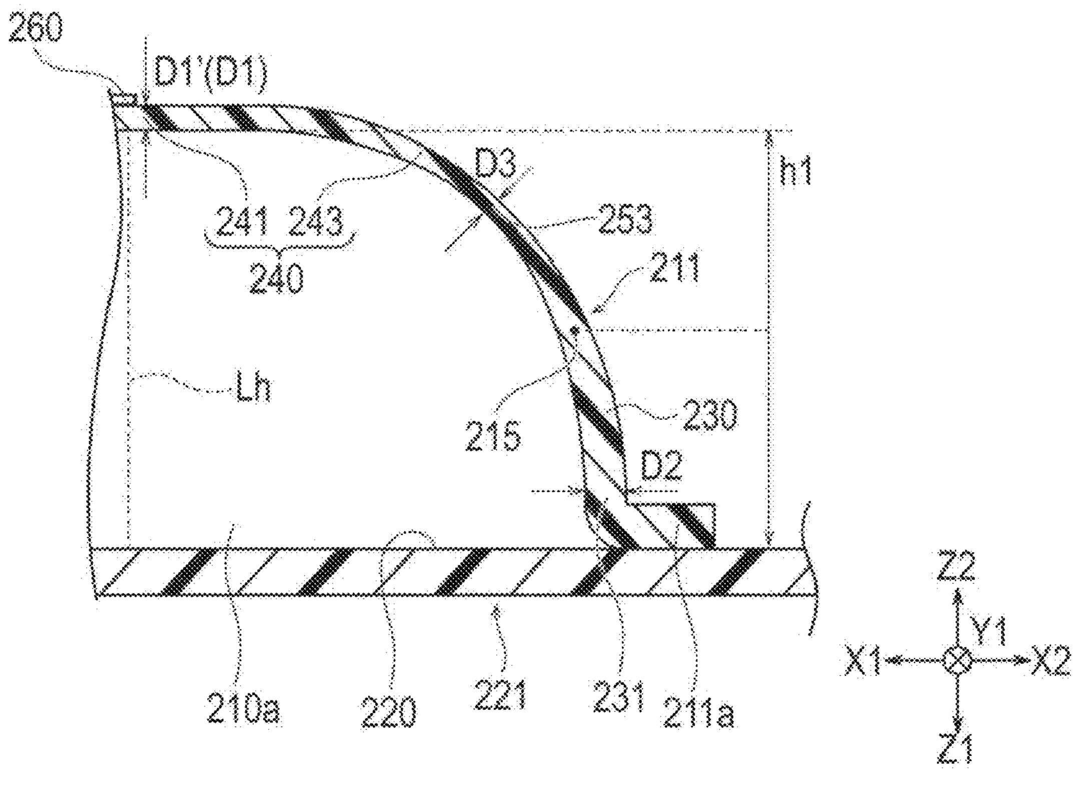
FIG. 17 is an enlarged view of part of the cross-sectional view illustrated in FIG. 15.

FIGS. 10 to 22 are views for explaining each portion of the inflatable portion 210. FIG. 10 is a plan view of the inflatable portion 210, FIG. 11 is a perspective view of the inflatable portion 210, FIG. 12 is a front view of the inflatable portion 210 seen from a direction of the arrow 12 in FIG. 11, and FIG. 13 is a partial cross-sectional view of the inflatable portion 210 (a cross-sectional view taken along the section line 13-13 in FIG. 11; in the specification, also described as a "cross-sectional view along a short axis A2"), FIG. 14 is a side view of the inflatable portion 210 seen from a direction of an arrow 14A illustrated in FIG. 11, FIG. 15 is a partial cross-sectional view of the inflatable portion 210 (a cross-sectional view taken along the section line 15-15 in FIG. 11; in the specification, also described as a "cross-sectional view along a long axis A1"), FIG. 16 is an enlarged view of part of the cross-sectional view illustrated in FIG. 13, and FIG. 17 is an enlarged view of part of the cross-sectional view illustrated in FIG. 15. FIGS. 10 to 17 illustrate the inflatable portion 210 in an inflated state.

Figure 20:
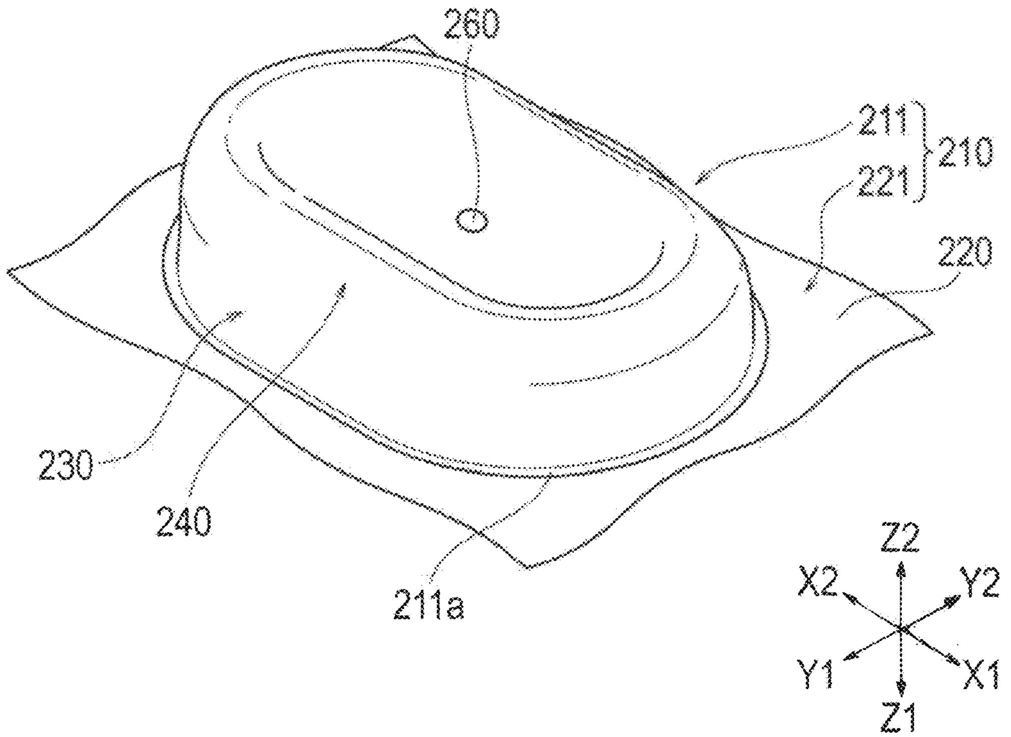
FIG. 20 is a perspective view illustrating a state when the inflatable portion in the inflated state is deflated.
Figure 21:
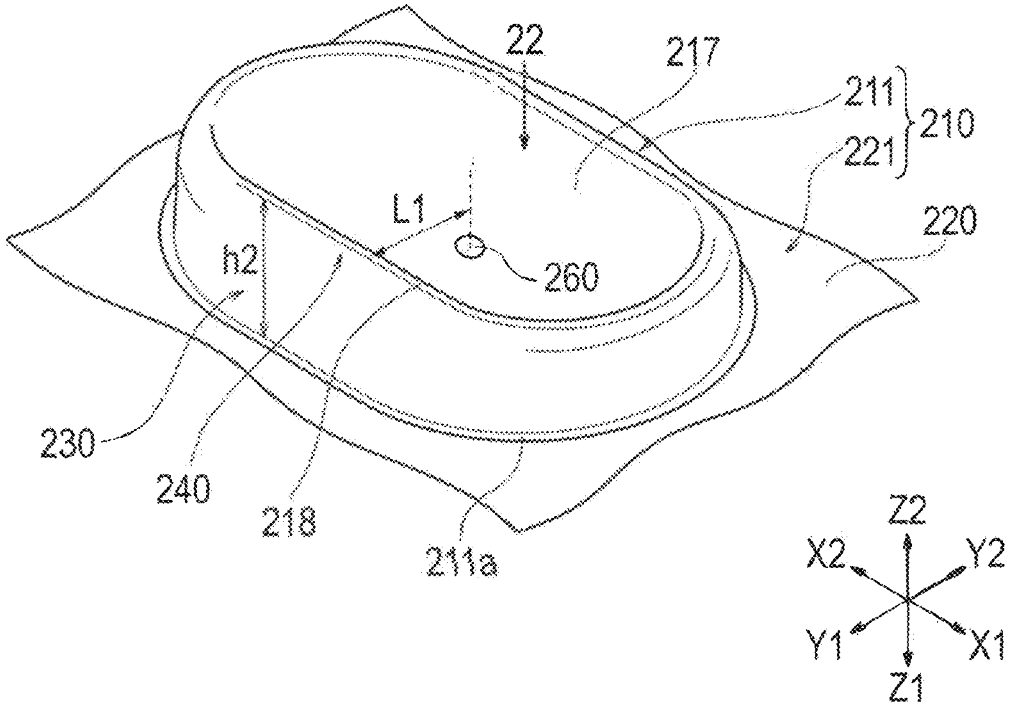
FIG. 21 is a perspective view illustrating the inflatable portion in a deflated state.
Figure 22:
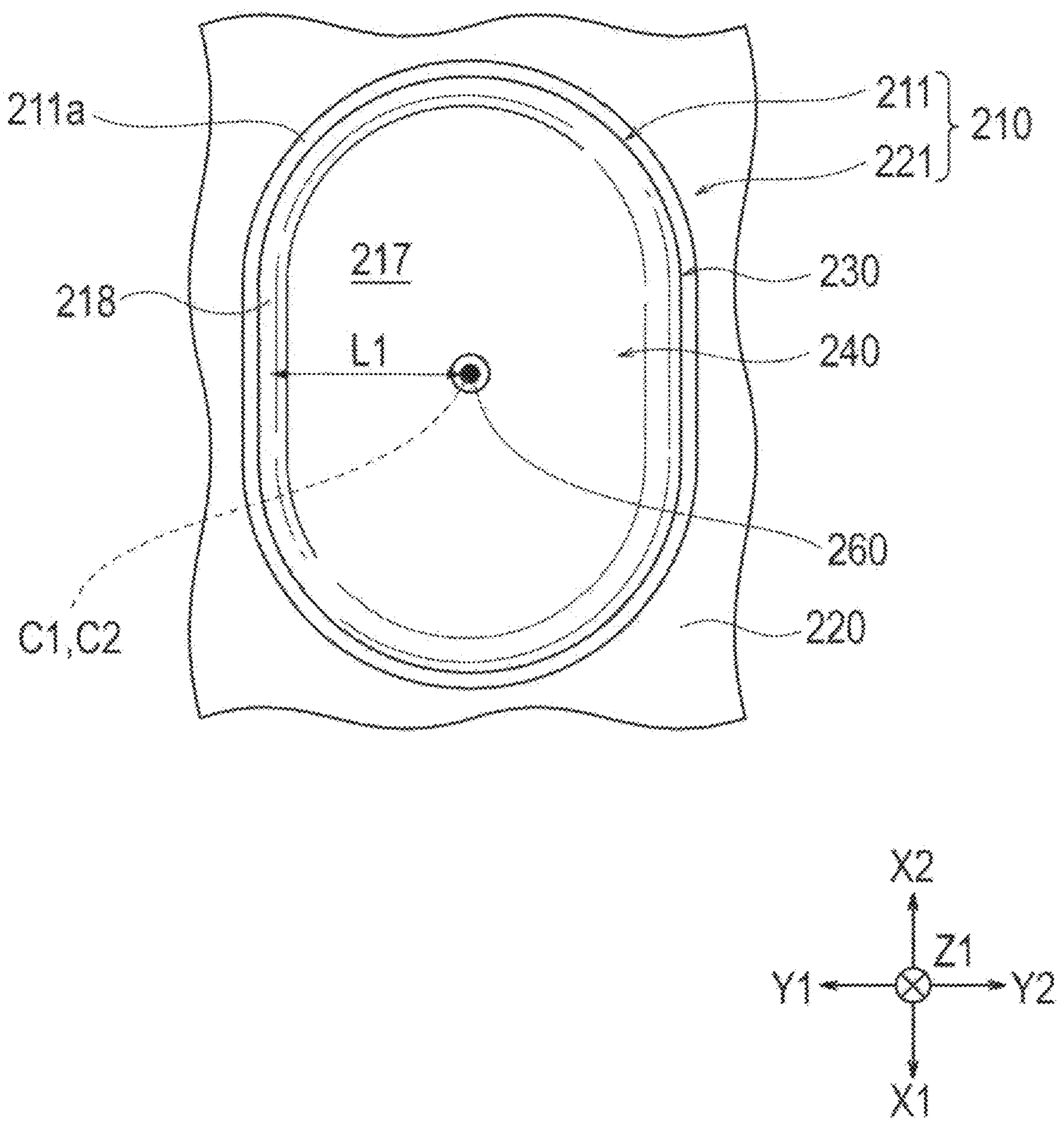
FIG. 22 is a plan view of the inflatable portion seen from a direction of an arrow 22 in FIG. 21.

FIGS. 18 to 21 are perspective views illustrating a state in which the inflatable portion 210 in the inflated state is deflated. FIG. 22 is a plan view of the inflatable portion 210 seen from a direction of an arrow 22A illustrated in FIG. 21.

Arrows X1 to X2 in the drawings indicate a longitudinal direction (a direction along the long axis A1) of the inflatable portion 210, arrows Y1 to Y2 in the drawings indicate a lateral direction (a direction along the short axis A2) of the inflatable portion 210, and arrows Z1 to Z2 in the drawings indicate a height direction when the inflatable portion 210 is inflated.

As illustrated in FIGS. 6, 13, and 15, the inflatable portion 210 can be constituted by an inflatable member such as a balloon including a lumen 210*a* into which a fluid such as air can flow.

As illustrated in FIGS. 13, 15, 16, and 17, the inflatable portion 210 has a bottom surface portion 220, a column portion 230 rising (extending or upstanding) from the bottom surface portion 220, and a curved surface portion 240 forming an upper surface of the column portion 230 in the inflated state.

A thickness D1 of the curved surface portion 240 is formed to be thinner than a thickness D2 of the column portion 230.

In the present embodiment, the thickness D1 at all sites of the curved surface portion 240 is formed to be thinner than the thickness D2 at all sites of the column portion 230. The thickness D1 of the curved surface portion 240 can be defined by the largest thickness of the portion forming the curved surface portion 240. In the present embodiment, a thickness D1' of a top surface portion 241 is the largest in the curved surface portion 240. Thus, the thickness D1 of the curved surface portion 240 is defined by the thickness D1' of the top surface portion 241.

The thickness D2 of the column portion 230 can be defined by the largest thickness of the portion forming the column portion 230. In the present embodiment, the thickness D2 of the column portion 230 is largest at a root portion 231 (see FIGS. 16 and 17) of the column portion 230 connected to an edge portion 211*a*. Thus, the thickness D2 of the column portion 230 is defined by the thickness of the root portion 231 of the column portion 230.

As illustrated in FIGS. 6, 13, and 15, the inflatable portion 210 includes a sheet member 211 and a sheet-like or sheet-shaped connection member 221 connected to a main body portion 110 of the cover member 100.

As illustrated in FIGS. 13, 15, 16, and 17, the sheet member 211 constitutes the column portion 230 and the curved surface portion 240 of the inflatable portion 210. The sheet member 211 is preferably molded so as to form the column portion 230 and the curved surface portion 240 of the inflatable portion 210 in a state where the inflatable portion 210 is inflated.

As illustrated in FIGS. 13, 15, 16, and 17, an inner surface (a surface located on a lumen 210*a* side) of the connection member 221 constitutes the bottom surface portion 220 of the inflatable portion 210. The bottom surface portion 220 includes a region located closer to the center in a plane direction (center C1, C2 side described later) than a region Pr (see FIGS. 10, 13, and 15) where the outer surface of the column portion 230 located along a circumferential direction of the inflatable portion 210 is projected in the connection member 221.

The edge portion 211*a* of the sheet member 211 is connected to the connection member 221. A space defined between the sheet member 211 and the connection member 221 constitutes the lumen 210*a*. The sheet member 211 and the connection member 221 can be connected by, for example, fusion bonding or an adhesive.

For example, the inflatable portion 210 can be constituted by two sheet-like or sheet-shaped members. In a case where the inflatable portion 210 is constituted in this manner, the inflatable portion 210 can be constituted by connecting an edge portion of a first sheet-like member or sheet-shaped member to a second sheet-like member or sheet-shaped member in a state where the lumen 210*a* is formed between two sheet-like or sheet-shaped members of the first sheet-like member and the second sheet-like member. For example, as the first sheet-like member, it is possible to use the sheet member 211 molded so as to form the column portion 230 and the curved surface portion 240 of the inflatable portion 210 in a state where the inflatable portion 210 is inflated, and as the second sheet-like member, it is possible to use a planar sheet-like member forming the bottom surface portion 220 on one surface side (lumen 210*a* side).

The sheet member 211 and the connection member 221 constituting the inflatable portion 210 can be made of, for example, a resin material having a predetermined thickness. The material of the sheet member 211 and the connection member 221 is not particularly limited, and for example, polyvinyl chloride, polyethylene, polypropylene, polybutadiene, polyolefins such as ethylene-vinyl acetate copolymer (EVA), polyester such as polyethylene terephthalate (PET) or polybutylene terephthalate (PBT), various thermoplastic elastomers such as polyvinylidene chloride, silicone, polyurethane, polyamide elastomer, polyurethane elastomer or polyester elastomer, nylon, nylon elastomer, or any combination thereof (such as a blend resin, a polymer alloy and a laminate) can be used.

As illustrated in FIG. 6, the inflatable portion 210 is disposed on the inner surface 110*a* side of the main body portion 110 of the cover member 100.

The inner surface 110*a* of the main body portion 110 is a surface to be disposed on the body surface side of the right hand H1 when the hemostatic device 10 is attached to the right hand H1 (see FIG. 27). The outer surface 110*b* of the main body portion 110 is a surface located on the opposite side of the inner surface 110*a*.

As illustrated in FIG. 6, the connection member 221 is connected to the inner surface 110*a* of the main body portion 110 of the cover member 100. The inflatable portion 210 is connected to the main body portion 110 via the connection member 221. The connection member 221 can be connected to the main body portion 110 by, for example, fusion bonding or an adhesive.

The connection member 221 is disposed so as to form a space g between the connection member 221 and the cover member 100. A support member 300 to be described later is disposed in the space g.

As illustrated in FIGS. 10, 26, and 27, the inflatable portion 210 includes a marker portion (visually identifiable marker) 260 for aligning the inflatable portion 210 with the first puncture site p1.

In the plan view in the inflated state illustrated in FIG. 10, the bottom surface portion 220 includes two straight portions 223*a* and 223*b* facing each other across the marker portion 260, and curved portions 224*a* and 224*b* facing each other across the marker portion 260 and connecting the two straight portions 223*a* and 223*b*. Thus, the side surfaces of the column portion 230 on the straight portions 223*a* and 223*b* side are formed straighter than the side surfaces of the column portion 230 on the curved portions 224*a* and 224*b* side in a state where the inflatable portion 210 is inflated.

The bottom surface portion 220 has the long axis A1 passing through the center C1 of the bottom surface portion 220 in the lateral direction (the direction of arrows Y1 to Y2) and the short axis A2 passing through the center C2 of the bottom surface portion 220 in the longitudinal direction (the direction of arrows X1 to X2) and shorter than the long axis A1 in the inflated state of the inflatable portion 210.

A thickness of the inflatable portion 210 is formed to be bilaterally symmetrical with respect to the long axis A1. The thickness of the inflatable portion 210 is formed to be vertically symmetrical with respect to the short axis A2.

In the present embodiment, the inflatable portion 210 has a substantially oval shape rotationally symmetric with respect to the centers C1 and C2 in the plan view in the inflated state illustrated in FIG. 10.

As illustrated in FIGS. 6, 13, 15, 16, and 17, the marker portion 260 is disposed on the outer surface of the top surface portion 241. For example, the marker portion 260 may be disposed on an inner surface of the top surface portion 241 (a surface facing the lumen 210*a*).

The marker portion 260 includes a transparent central portion surrounding the centers C1 and C2 and a colored circular frame portion surrounding the central portion.

A specific shape and color of the marker portion 260, a position of the marker portion 260 in the plane direction of the inflatable portion 210, a forming method, and the like, are not particularly limited. The marker portion 260 can also be formed of, for example, a circular marker in which the entire portion is formed in color, a marker constituted with a transparent central portion and a rectangular frame portion, a rectangular marker in which the entire portion is formed in color, or the like.

As illustrated in FIGS. 16 and 17, the curved surface portion 240 includes the top surface portion 241 where the marker portion 260 is located, and an inclined portion 243 located around (surrounding) the top surface portion 241 and connected to the column portion 230.

The top surface portion 241 includes a top portion that inflates to a position farthest from the bottom surface portion 220 side in a state where the inflatable portion 210 is inflated.

The inclined portion 243 is inclined from the top surface portion 241 side toward the column portion 230 side in the cross-sectional views illustrated in FIGS. 16 and 17. The inclined portion 243 is inclined with respect to a perpendicular line Lh connecting the bottom surface portion 220 and the top surface portion 241.

The inclined portion 243 has a thin (thinned) portion 253 that surrounds the top surface portion 241 and is formed to be thinner than a thickness of the top surface portion 241. In the present embodiment, the thin portion 253 constitutes a portion having the thinnest thickness in the curved surface portion 240.

As illustrated in FIGS. 13, 15, 16, and 17, the thin portion 253 is disposed so as to surround the entire circumference of the top surface portion 241. In other words, the thin portion 253 is disposed concentrically with the top surface portion 241.

The thin portion 253 is located at a position that is point symmetrical about the marker portion 260.

The marker portion 260 is located at a position where the center C1 of the long axis A1 overlaps with the center C2 of the short axis A2. The thin or thinned portion 253 is disposed concentrically with the top surface portion 241 so as to surround the circumference of the marker portion 260.

The term "concentric" in the present specification means that the center position is common in the plan view illustrated in FIG. 10 and the outer shapes have substantially the same shape or similar shapes. In other words, two or more portions defined as concentrically are not limited to a circular shape. For example, the top surface portion 241 having an oval shape in the plan view of FIG. 10 and the thin portion 253 having an oval shape located so as to surround the circumference of the top surface portion 241 can be defined as being concentrically disposed with respect to the respective centers C1 and C2.

As illustrated in FIGS. 16 and 17, the inflatable portion 210 forms a first height h1 between the bottom surface portion 220 and the top surface portion 241 in a state where the inflatable portion 210 is inflated. The thin portion or thinned portion 253 is located closer to the top surface portion 241 than an intermediate position 215 of the first height h1.

As illustrated in FIGS. 16 and 17, the first height h1 is a distance between the bottom surface portion 220 and the top surface portion 241 (inner surface of the connection member 221).

As illustrated in FIGS. 16 and 17, in the inflatable portion 210, the thickness D2 of the column portion 230 is the largest in a state where the inflatable portion 210 is inflated. The thickness of the inflatable portion 210 gradually decreases from the root portion 231 side of the column portion 230 toward the intermediate position 215, and the thickness becomes the thinnest at the thin portion 253 located closer to the top surface portion 241 than the intermediate position 215. In addition, the thickness of the inflatable portion 210 gradually increases from the thin portion 253 toward the top surface portion 241. In the inflatable portion 210, the thickness of the top surface portion 241 and the thickness of a boundary portion transitioning from the column portion 230 to the curved surface portion 240 are the largest in a portion except the column portion 230 among the respective portions constituted by the sheet member 211. In the present embodiment, the thickness of the top surface portion 241 is substantially the same as the thickness of the boundary portion transitioning from the column portion 230 to the curved surface portion 240.

The first height h1 of the inflatable portion 210 can be formed to be, for example, 12 mm to 16 mm.

In a case where the first height h1 is 12 mm to 16 mm, the column portion 230 can be formed such that a ratio of a distance from the bottom surface portion 220 with respect to the first height h1 falls within a range from 0% to 50%. Further, a boundary between the column portion 230 and the inclined portion 243 can be formed such that a ratio of a distance from the bottom surface portion 220 with respect to the first height h1 falls within a range from 20% to 50%.

In addition, in a case where the first height h1 is 12 mm to 16 mm, the inclined portion 243 can be formed such that a ratio of a distance from the bottom surface portion 220 with respect to the first height h1 falls within a range from 20% to 95%. Further, a boundary between the inclined portion 243 and the top surface portion 241 can be formed such that a ratio of a distance from the bottom surface portion 220 with respect to the first height h1 falls within a range from 80% to 95%.

Further, in a case where the first height h1 is 12 mm to 16 mm, the thin portion 253 can be formed such that a ratio of the distance from the bottom surface portion 220 with respect to the first height h1 falls within a range from 60% to 80%.

The thin portion 253 is located at the inclined portion 243.

In a case where the first height h1 is 12 mm to 16 mm, the top surface portion 241 can be formed such that a ratio of a distance from the bottom surface portion 220 with respect to the first height h1 falls within a range from 80% to 100%.

The inflatable portion 210 is configured such that a magnitude relationship of the thicknesses of the column portion 230, the curved surface portion 240, the top surface portion 241, the inclined portion 243, and the thin portion 253 (the thickness D2 of the column portion 230 is larger than the thickness D1 of the curved surface portion 240, and the thickness D3 of the thin portion 253 is smaller than the thickness D1 of the top surface portion 241) is satisfied in both the cross-sectional views along the short axis A2 illustrated in FIGS. 13 and 16 and the cross-sectional views along the long axis A1 illustrated in FIGS. 15 and 17. In other words, the inflatable portion 210 satisfies the above thickness relationship in the curved portions **224*a* and 224*b* located on both sides in a vertical direction with reference to the short axis A2 illustrated in FIG. 10 and also satisfies the above thickness relationship in the straight portions 223*a* and 223*b* located on both sides in a horizontal direction with reference to the long axis A1 illustrated in FIG. 10**.

Next, with reference to FIGS. 18 to 22, operational effects of the inflatable portion 210 and behavior when the inflatable portion 210 inflates and deflates will be described.

The inflatable portion 210 forms the first height h1 between the bottom surface portion 220 and the top surface portion 241 in a state where the inflatable portion 210 is inflated (see FIGS. 16 and 17). The thin or thinned portion 253 is located closer to the top surface portion 241 than the intermediate position 215 of the first height h1. The thin or thinned portion 253 of the inflatable portion 210 is located closer to the top surface portion 241 than the intermediate position 215, and thus, when the inflatable portion 210 starts inflating, the thin portion 253 serves as a starting point of the inflating, and the inflating on the top surface portion 241 side progresses more quickly than the inflating on the column portion 230 side. Thus, when the inflatable portion 210 inflates, the inflatable portion 210 can prevent the inflating from progressing on the column portion 230 side. If the column portion 230 inflates and the column portion 230 inflates in the lateral direction, the first height h1 corresponding to the maximum inflating height when the inflatable portion 210 inflates decreases. As a result, a compressive force to be applied to the first puncture site p1 by the inflatable portion 210 decreases. In the hemostatic device 10, it is possible to prevent decrease of the compressive force as described above.

The bottom surface portion 220 has two straight portions 223*a* and 223*b* facing each other across the marker portion 260 and the two curved portions 224*a* and 224*b* facing each other across the marker portion 260 and connecting two straight portions 223*a* and 223*b* in a state where the inflatable portion 210 is inflated (see FIG. 10). Accordingly, the column portion 230 rising (extending or upstanding) from the bottom surface portion 220 has an outer shape similar to that of the bottom surface portion 220 when an outer surface of the column portion 230 is projected onto the connection member 221. In other words, the inflatable portion 210 of the hemostatic device 10 has a predetermined region extending in the lateral direction between the two straight portions 223*a* and 223*b* connected by the two curved portions 224*a* and 224*b*. Thus, when the inflatable portion 210 applies a compressive force to the first puncture site p1, the hemostatic device 10 can form an area of the inflatable portion 210 (an area of the top surface portion 241) to a predetermined size or more. This makes it possible for the inflatable portion 210 to firmly apply a compressive force to the first puncture site p1. In addition, in the inflatable portion 210, the area of the inflatable portion 210 is secured to a predetermined size, and thus, even when the inflatable portion 210 is displaced from the first puncture site p1, the compressive force is less likely to decrease due to influence of displacement of the inflatable portion 210. As a result, even if the inflatable portion 210 is slightly displaced from the first puncture site p1, the compressive force can be appropriately applied. In the inflatable portion formed in an oval shape without the straight portions 223*a* and 223*b*, even if the dimensions in the lateral direction and the longitudinal direction are formed to be similar to those of the inflatable portion 210, a radius of curvature of the portion corresponding to the curved portion between a maximum dimension position in the lateral direction and a maximum dimension position in the longitudinal direction becomes small, and thus, the compressed area becomes smaller than an area compressed by the inflatable portion 210. Thus, the inflatable portion 210 of the present embodiment can secure a larger compressed area than an area when the inflatable portion is formed in an oval shape.

Figure 18:
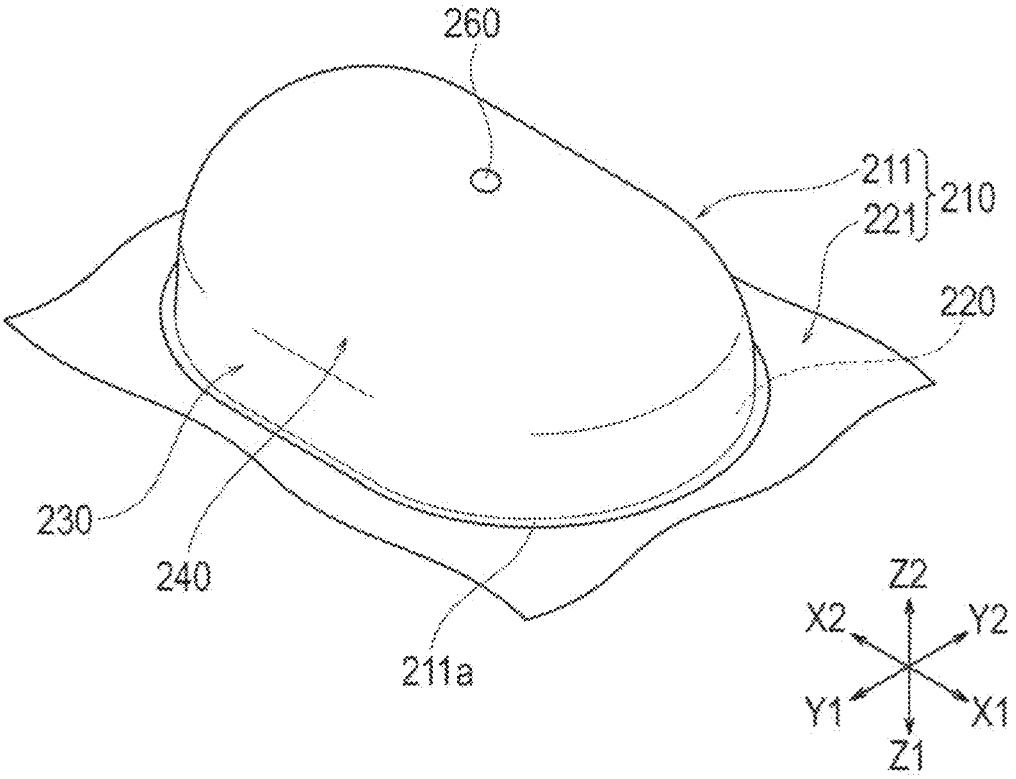
FIG. 18 is a perspective view of the inflatable portion in the inflated state.
Figure 19:
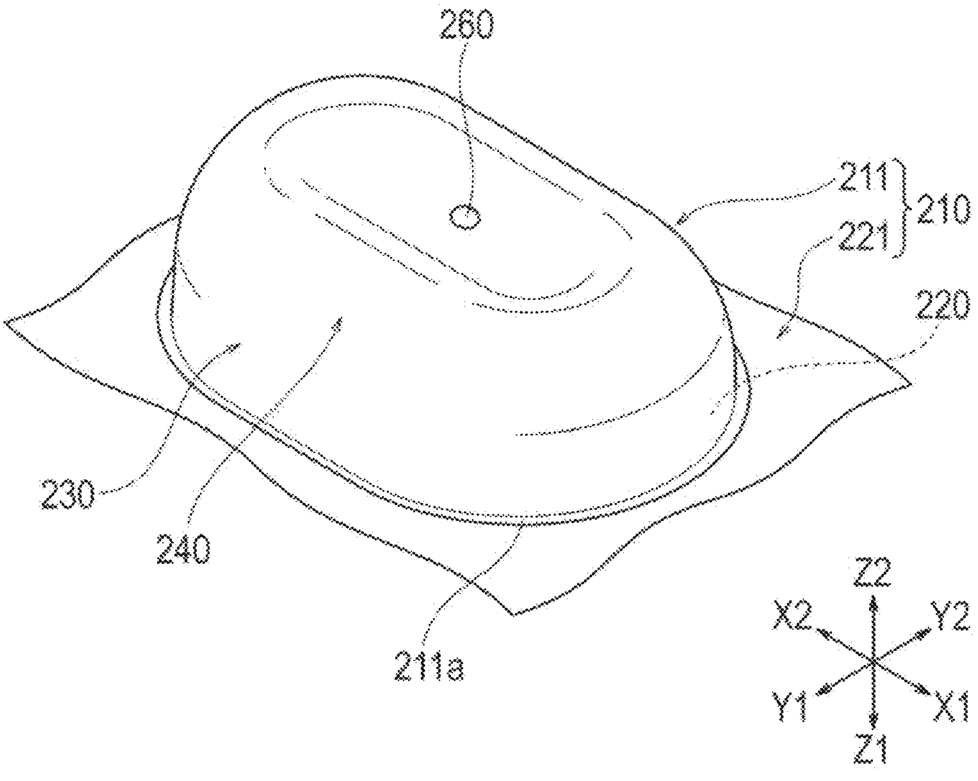
FIG. 19 is a perspective view illustrating a state when the inflatable portion in the inflated state is deflated.

FIG. 18 illustrates the inflatable portion 210 in the inflated state. FIG. 19 to FIG. 20 illustrate a state when deflating of the inflatable portion 210 is started and progresses from a state illustrated in FIG. 18. FIGS. 21 and 22 illustrate a state when the inflatable portion 210 is deflated.

The curved surface portion 240 is thinner than the column portion 230 (see FIGS. 16 and 17). Thus, as illustrated in FIGS. 19 and 20, when the inflatable portion 210 deflates, the curved surface portion 240 deforms so as to approach the bottom surface portion 220 while maintaining a state in which the column portion 230 rises with respect to the bottom surface portion 220.

The thin portion 253 of the inclined portion 243 is thinner than the top surface portion 241 where the marker portion 260 is located (see FIGS. 16 and 17). Thus, when the inflatable portion 210 deflates, the thin portion 253 formed to have the thinnest thickness in the curved surface portion 240 serves as a starting point of deformation.

In an initial stage where deflating of the inflatable portion 210 is started, while deformation is started such that the thin portion 253 is bent toward the bottom surface portion 220, the top surface portion 241 having a larger thickness than the thin portion 253 moves so as to approach the bottom surface portion 220 while preventing a surface shape from being greatly impaired due to the deformation of the thin portion 253. It is therefore possible to prevent the marker portion 260 located on the top surface portion 241 from being displaced in a plane direction of the top surface portion 241 when the inflatable portion 210 deflates.

The top surface portion 241 is thicker than the thin portion 253. Thus, the inflatable portion 210 can prevent the top surface portion 241 from being excessively crushed when the top surface portion 241 applies a compressive force to the first puncture site p1 in a state where the inflatable portion 210 is inflated. Thus, the inflatable portion 210 can effectively apply a compressive force from the top surface portion 241 to the first puncture site p1.

The thin portion or thinned portion 253 is disposed so as to surround the entire circumference of the top surface portion 241 (see FIGS. 13 and 15). Thus, when the inflatable portion 210 starts to deflate, as illustrated in FIG. 19, the thin portion 253 surrounding the entire circumference of the top surface portion 241 serves as a starting point of deformation. The inflatable portion 210 deflates in a state where the entire circumference of the top surface portion 241 is surrounded by the thin portion 253, so that it is possible to prevent the surface shape of the top surface portion 241 located closer to the centers C1 and C2 than the thin portion 253 at the time of deflating from being impaired. It is therefore possible to prevent the marker portion 260 located on the top surface portion 241 from being displaced in the plane direction of the top surface portion 241 when the inflatable portion 210 deflates.

The thin portion or thinned portion 253 is located at a position that is point symmetrical about the marker portion 260 (see FIG. 10). Thus, the inflatable portion 210 can maintain a relative positional relationship between the marker portion 260 and the thin or thinned portion 253 without being affected by an attachment position and a direction of the inflatable portion 210 with respect to the right hand H1. Accordingly, in the hemostatic device 10, even when the inflatable portion 210 in a state where inflating and deflating have been repeated is aligned with the first puncture site p1 again, the relative positional relationship between the marker portion 260 and the thin portion 253 is suitably maintained, so that the marker portion 260 can be appropriately aligned with the first puncture site p1.

The bottom surface portion 220 has the long axis A1 which passes through the center C1 in the lateral direction of the bottom surface portion 220 and the short axis A2 which passes through the center C2 in the longitudinal direction of the bottom surface portion 220 and which is shorter than the long axis A1 in the inflated state of inflatable portion 210 (see FIG. 10). The thickness of the inflatable portion 210 is bilaterally symmetrical with respect to the long axis A1. The inflatable portion 210 can inflate bilaterally symmetrically with respect to the long axis A1, and thus, a difference in an inflating amount hardly occurs at a position in the horizontal direction with respect to the long axis A1. Accordingly, the inflatable portion 210 can apply a compressive force along a direction substantially perpendicular to the first puncture site p1. Furthermore, the inflatable portion 210 can inflate bilaterally symmetrically with respect to the long axis A1, so that the inflatable portion 210 is less likely to be displaced from the first puncture site p1 in the inflated state. For example, if the inflatable portion 210 is formed to have an asymmetric thickness in the horizontal direction with respect to the long axis A1, a magnitude of the force applied in the horizontal direction with respect to the long axis A1 of the inflatable portion 210 becomes different when the inflatable portion 210 inflates. Thus, the hemostatic device 10 cannot apply a compressive force in the vertical direction from the inflatable portion 210 to the first puncture site p1, and it becomes difficult to effectively stop bleeding.

In addition, the thickness of the inflatable portion 210 is bilaterally symmetrical with respect to the long axis A1, and thus, when the inflatable portion 210 deflates, the inflatable portion 210 deflates uniformly in the horizontal direction with reference to the long axis A1. Thus, when the inflatable portion 210 deflates, a relative positional relationship between the bottom surface portion 220 and the top surface portion 241 can be maintained. In particular, in the present embodiment, the marker portion 260 is located on the top surface portion 241, so that it is possible to prevent the marker portion 260 from being displaced in the plane direction due to deflating of the inflatable portion 210.

As illustrated in FIGS. 21 and 22, the inflatable portion 210 forms a recess 217 and a protrusion 218 surrounding the recess 217 in a state where the inflatable portion 210 is deflated.

The protrusion 218 is formed by the column portion 230. In a state where the recess 217 and the protrusion 218 are formed, the top surface portion 241 is located in the recess 217.

In the inflatable portion 210, the top surface portion 241 on which the marker portion 260 is located is disposed in the recess 217 in a state where the inflatable portion 210 is deflated. The protrusion 218 surrounding the recess 217 applies tension so as to pull the recess 217 to the circumference. This makes wrinkles and twists less likely to occur in the recess 217. In the hemostatic device 10, when the inflatable portion 210 is disposed on the right hand H1, the marker portion 260 is disposed along the surface of the top surface portion 241 with less wrinkles and twists. Thus, in the hemostatic device 10, the marker portion 260 can be easily aligned with the first puncture site p1. In addition, in the hemostatic device 10, it is possible to prevent decrease in visibility of the marker portion 260 located in the recess 217 and visibility of the first puncture site p1 that is to be confirmed through the recess 217 as a result of wrinkles and twists being less likely to occur in the recess 217. Thus, in the hemostatic device 10, the marker portion 260 can be more easily aligned with the first puncture site p1.

As illustrated in FIGS. 21 and 22, a height h2 of the protrusion 218 is shorter (less) than the distance L1 from a top portion of the protrusion 218 (the position protruding in a height direction) to a center of the bottom surface portion 220 in the plane direction. The center of the bottom surface portion 220 in the plane direction is a position where the center C1 of the bottom surface portion 220 in the lateral direction intersects with the center C2 of the bottom surface portion 220 in the longitudinal direction.

In the hemostatic device 10, the height h2 of the protrusion 218 is shorter (less) than the distance L1, so that it is possible to prevent the protrusion 218 from overlapping the center of the bottom surface portion 220 even if the protrusion 218 falls down toward the recess 217 as a result of the protrusion 218 coming into contact with the body surface of the right hand H1 when the inflatable portion 210 in the deflated state is attached to the right hand H1. This makes it possible for the operator to appropriately dispose the center of the top surface portion 241 at the first puncture site p1. In the hemostatic device 10, the marker portion 260 is disposed at the center of the top surface portion 241, so that it is possible to prevent the protrusion 218 from overlapping the marker portion 260 even when the protrusion 218 falls down toward the recess 217 side. This makes it possible for the operator to appropriately dispose the inflatable portion 210 at the first puncture site p1 based on the marker portion 260.

Figure 24:
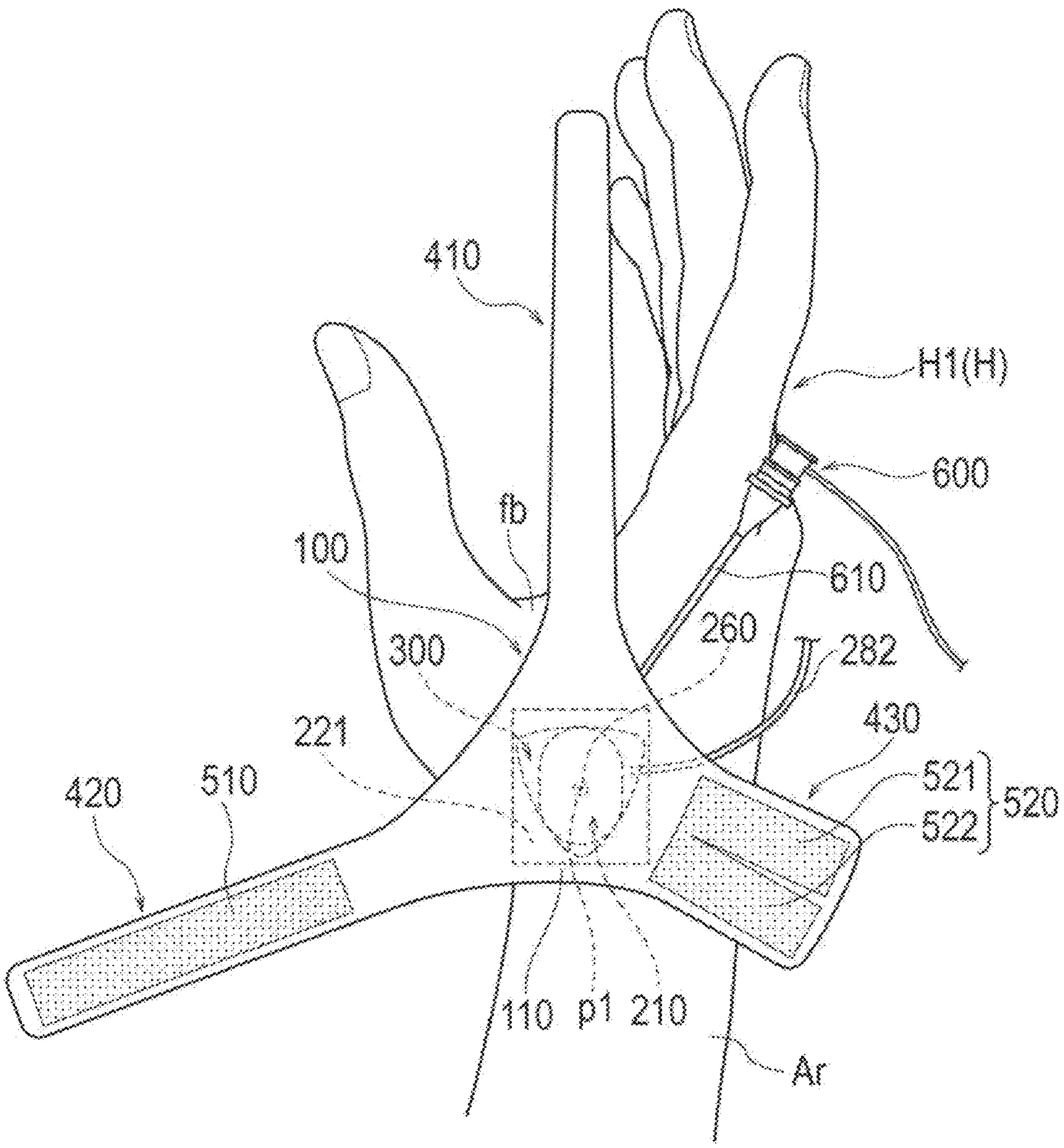
FIG. 24 is a view schematically illustrating a use example of the hemostatic device.

To start hemostasis using the hemostatic device 10, the operator disposes the inflatable portion 210 in the deflated state at the first puncture site p1 (see FIG. 24). After the operator disposes the inflatable portion 210 at the first puncture site p1, the operator inflates the inflatable portion 210. The inflatable portion 210 applies a compressive force to the first puncture site p1 by the inflating of the inflatable portion 210. After the operator inflates the inflatable portion 210 and starts hemostatic compression, for example, in a case where the compressive force is not appropriately applied from the inflatable portion 210 to the first puncture site p1 due to influence of the arrangement (positioning) of the inflatable portion 210, or the like, the operator adjusts the arrangement of the inflatable portion 210 again. When adjusting the arrangement of the inflatable portion 210 again, the operator deflates the inflatable portion 210. As a result of the operator deflating the inflatable portion 210, a state where the inflatable portion 210 applies the compressive force to the first puncture site p1 is resolved, and thus, the operator can adjust the arrangement of the inflatable portion 210 again. However, if the inflatable portion 210 is deflated after the inflatable portion 210 has been inflated once, there is a case where the inflatable portion 210 does not deform to the same shape as the initial shape. For example, in the inflatable portion 210, in a case where the thickness of the inflatable portion 210 is uniformly formed, an internal pressure of the inflatable portion 210 is uniformly applied to the entire inflatable portion 210, and thus, regularity is less likely to occur in the behavior of each portion of the inflatable portion 210 when the inflatable portion 210 inflates and deflates. Thus, in the inflatable portion 210, a portion serving as a starting point of deformation at the time of starting inflating and deflating becomes random at each time of inflating and deflating, and a shape at the time of deflating becomes also different at each time of deflating. Accordingly, in the hemostatic device 10, if the operator tries to align the inflatable portion 210 in the deflated state with the first puncture site p1 again after deflating the inflatable portion 210 that has been once inflated, it may be difficult to appropriately dispose a portion (for example, the top surface portion 241 on which the marker portion 260 is located) of the inflatable portion 210 at the first puncture site p1. In such a case, in order to align the portion of the inflatable portion 210 with the first puncture site p1, the operator performs deforms the inflatable portion 210 to a shape close to the initial shape by pressing the outer surface (liquid contact portion) of the inflatable portion 210 to be disposed at the first puncture site p1 with the fingers while deflating the inflatable portion 210. The operator deforms the inflatable portion 210 while touching the inflatable portion with the fingers in this manner, and then disposes the inflatable portion 210 again at the first puncture site p1. However, if the fingers touch the inflatable portion 210, there is a high possibility that blood flowing from the first puncture site p1 unnecessarily adheres to the outer surface of the inflatable portion 210 or contamination occurs at the first puncture site p1.

The hemostatic device 10 can prevent the above-described problem from occurring by exhibiting the following operational effects.

In the hemostatic device 10, the thickness D2 of the column portion 230 rising or extending from the bottom surface portion 220 of the inflatable portion 210 is larger than the thickness D1 of the curved surface portion 240 forming the upper surface of the column portion 230 (see FIGS. 16 and 17). Thus, in the hemostatic device 10, when the inflatable portion 210 inflates, the curved surface portion 240 forming the upper surface of the column portion 230 starts inflating earlier than the column portion 230. In addition, in the hemostatic device 10, when the inflatable portion 210 deflates, the curved surface portion 240 located at a position farther away from the bottom surface portion 220 than the column portion 230 starts deflating earlier than the column portion 230. As described above, in the hemostatic device 10, a starting point of deformation at the time of inflating and deflating is determined such that inflating is started from the curved surface portion 240 earlier than the column portion 230 when the inflatable portion 210 inflates, and deflating is started from the curved surface portion 240 earlier than the column portion 230 when the inflatable portion 210 deflates. Thus, the inflatable portion 210 has high restorability such that the inflatable portion 210 deforms to substantially the same shape as the initial shape when the inflatable portion 210 in the inflated state is deflated. Thereby, in the hemostatic device 10, a portion of the inflatable portion 210 can be easily aligned with the first puncture site p1, for example, when the inflatable portion 210 is aligned with the first puncture site p1 again after the inflatable portion 210 disposed at the first puncture site p1 in the inflated state is deflated. When changing the arrangement of the inflatable portion 210 with respect to the first puncture site p1, the operator does not need to perform an operation such as pressing the outer surface of the inflatable portion 210 with the fingers. Thus, when the inflatable portion 210 is aligned with the first puncture site p1 again, in the hemostatic device 10, it is possible to prevent the blood flowing from the first puncture site p1 from unnecessarily adhering to the outer surface of the inflatable portion 210 or prevent contamination at the first puncture site p1.

In particular, in the hemostatic device 10, even in the deflated state after the inflatable portion 210 has repeated inflating and deflating a plurality of times, a shape of the top surface portion 241 where the marker portion 260 serving as a mark for aligning the inflatable portion 210 with the first puncture site p1 is located is substantially the same as the initial shape. Thus, in the hemostatic device 10, it is possible to appropriately dispose the inflatable portion 210 at the first puncture site p1 based on the marker portion 260.

In addition, when the hemostatic device 10 is transported using an aircraft, or the like, it is conceivable that an air pressure in a space where the hemostatic device 10 is stored decreases due to an altitude of the aircraft, and the inflatable portion 210 unintentionally inflates due to change in the air pressure. As described above, the hemostatic device 10 has high restorability to the initial shape even after inflating and deflating a plurality of times. Thus, a state in which the marker portion 260 is located at the predetermined position of the top surface portion 241 is suitably maintained even when the hemostatic device 10 is started to be used in an actual medical site after the inflatable portion 210 inflates at the time of transportation on an aircraft, and thus, the inflatable portion 210 can be appropriately disposed at the first puncture site p1.

In addition, if the top surface portion 241 is formed to be excessively thick, it is conceivable that skin contact of the top surface portion 241 with respect to the body surface of the right hand H1 becomes worse and the patient feels pain when hemostatic compression is performed by the hemostatic device 10. In the hemostatic device 10, the thickness D1' of the top surface portion 241 is thinner than the thickness D2 of the column portion 230. Thus, in a state where the inflatable portion 210 is inflated, the skin contact of the top surface portion 241 with respect to the body surface of the right hand H1 becomes soft, and thus, the patient hardly feels pain.

In addition, in the hemostatic device 10, the thickness D2 of the column portion 230 is larger than the thickness D1' of the curved surface portion 240. Thus, in a state where the inflatable portion 210 is inflated, the root portion 231 of the column portion 230 deforms so as to rise in a direction substantially perpendicular to the bottom surface portion 220. As a result, the inflatable portion 210 can prevent the column portion 230 from tilting with respect to the bottom surface portion 220 when the inflatable portion 210 inflates. Thus, when the inflatable portion 210 inflates, the inflatable portion 210 can prevent the top surface portion 241 located on the curved surface portion 240 forming the upper surface of the column portion 230 from being displaced from the first puncture site p1. As a result, the hemostatic device 10 can stably apply a compressive force to the first puncture site p1 in a state where the inflatable portion 210 is inflated.

<Injection Portion>

Figure 1:
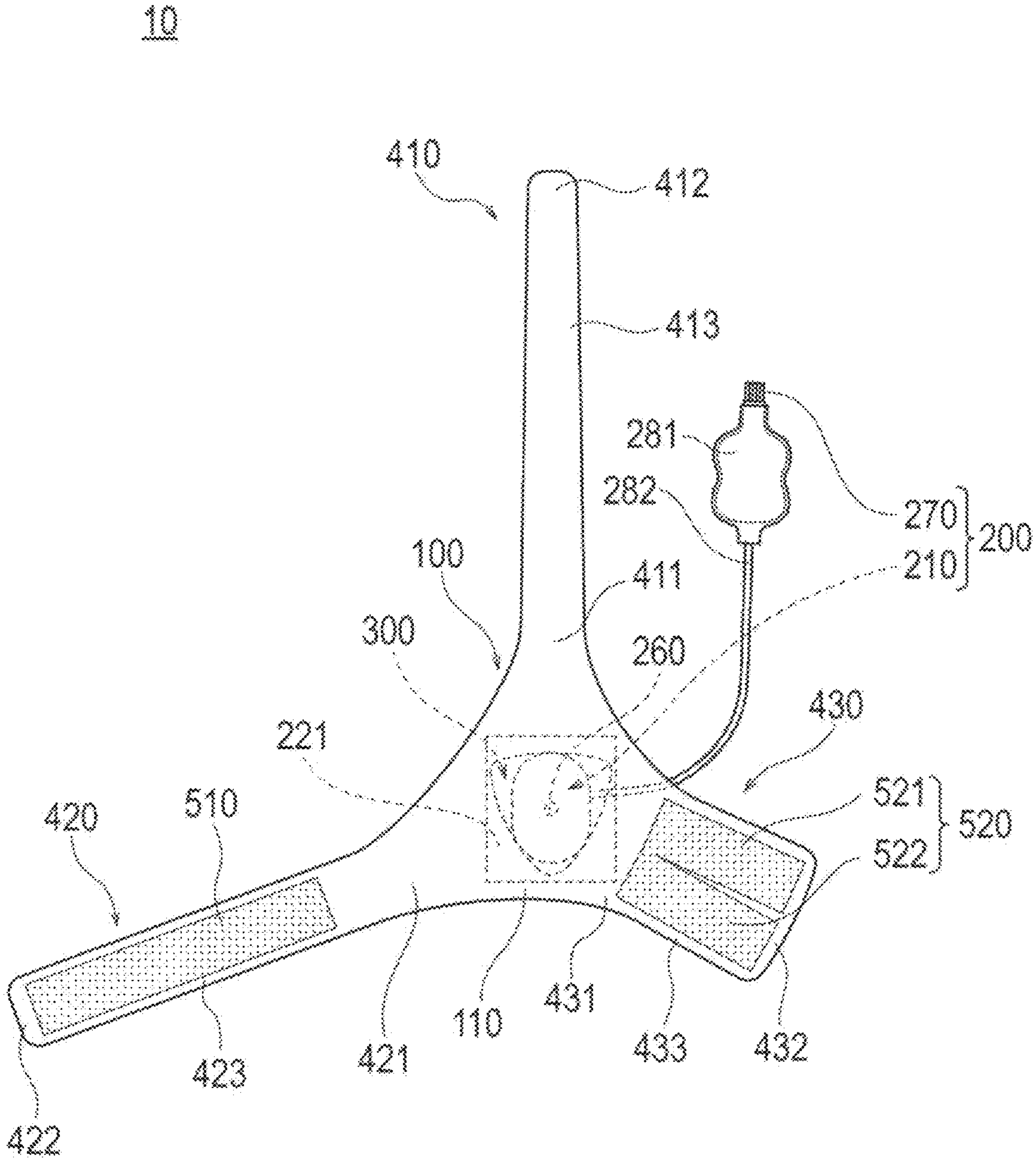
FIG. 1 is a view illustrating a hemostatic device according to an embodiment, and is a plan view seen from an outer surface side of each band body portion.
Figure 2:
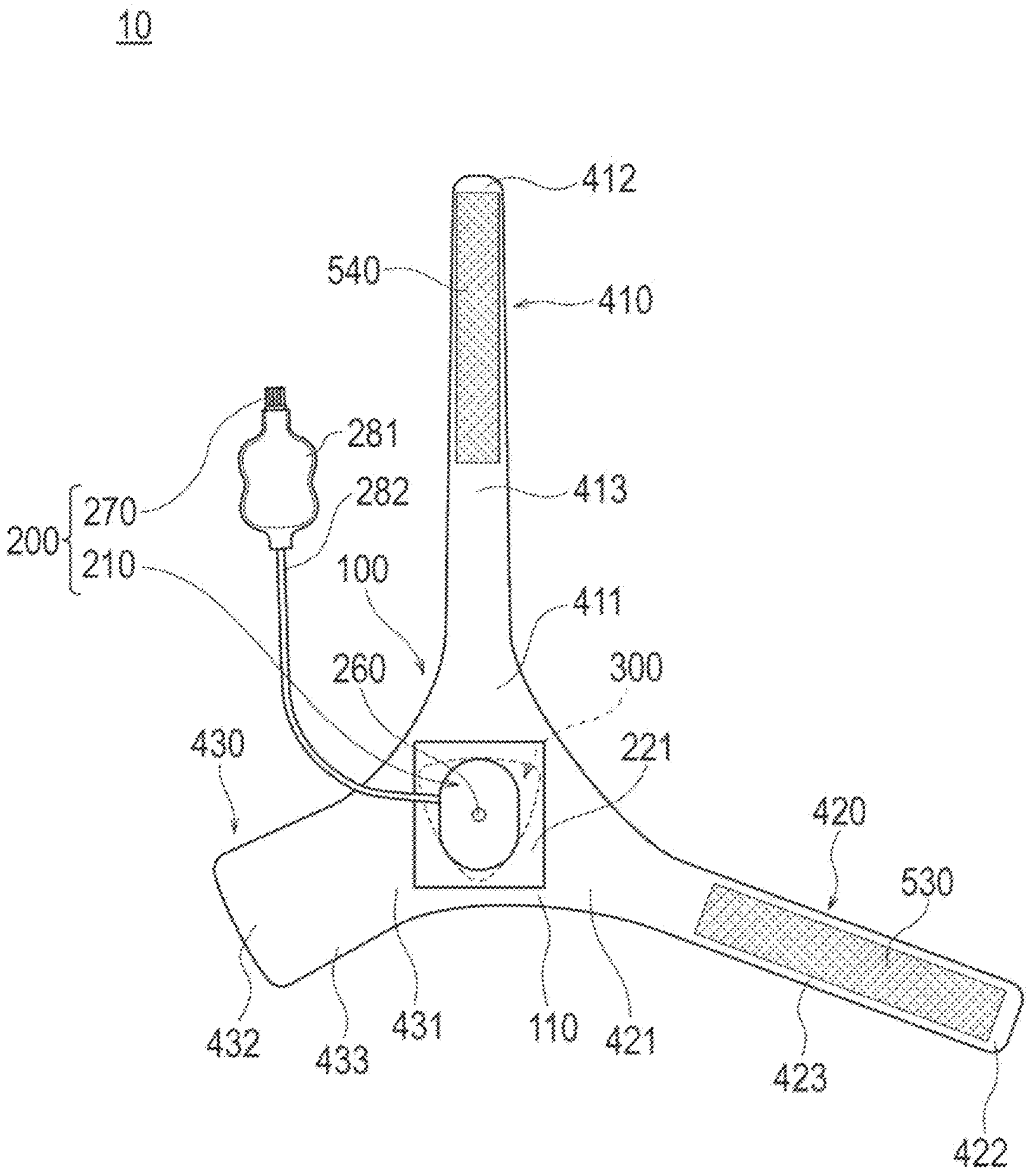
FIG. 2 is a view illustrating the hemostatic device according to the embodiment, and is a plan view seen from an inner surface side of each band body portion.
Figure 3:
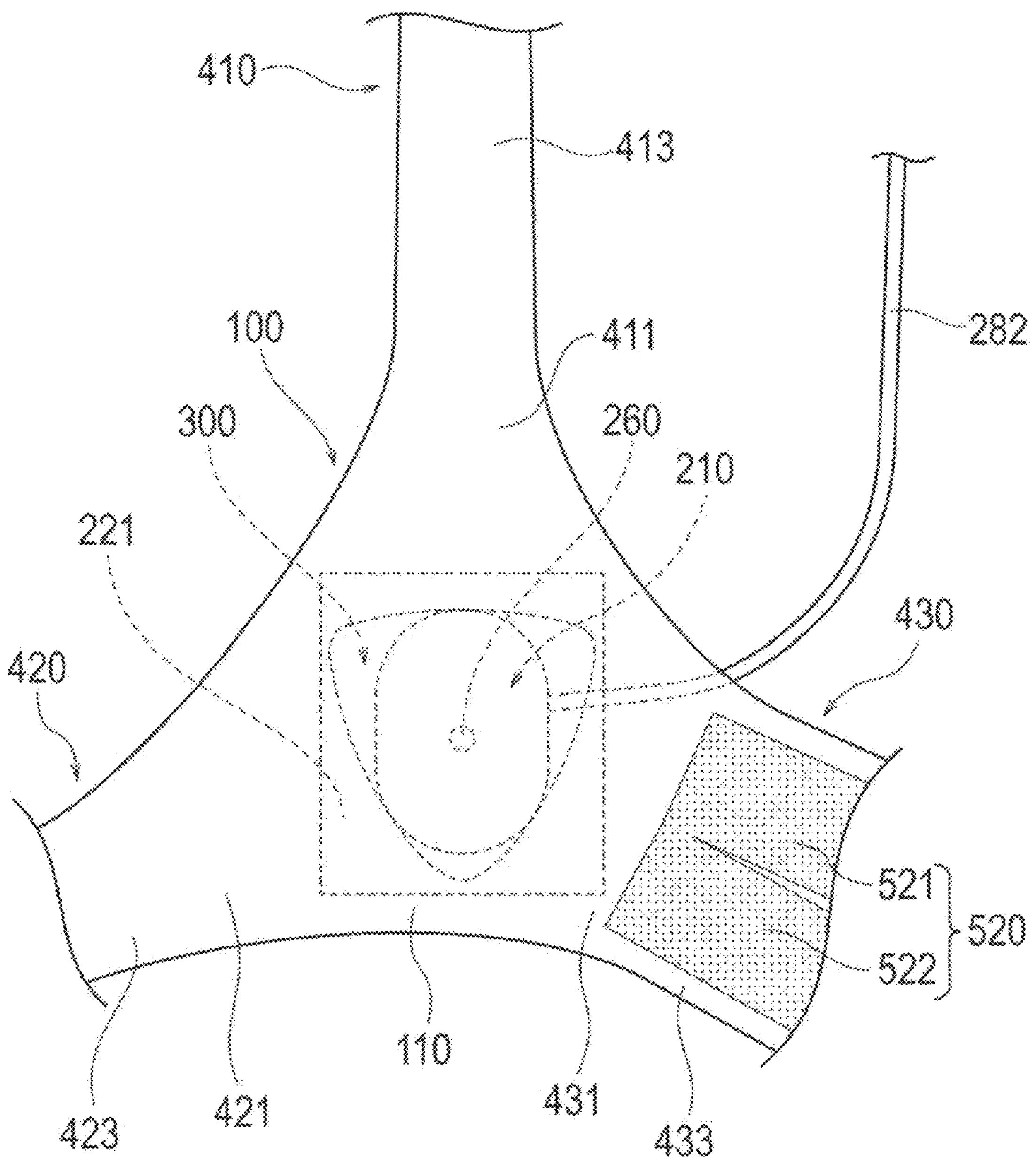
FIG. 3 is an enlarged view of part of the hemostatic device seen from an outer surface side of a cover member.
Figure 4:
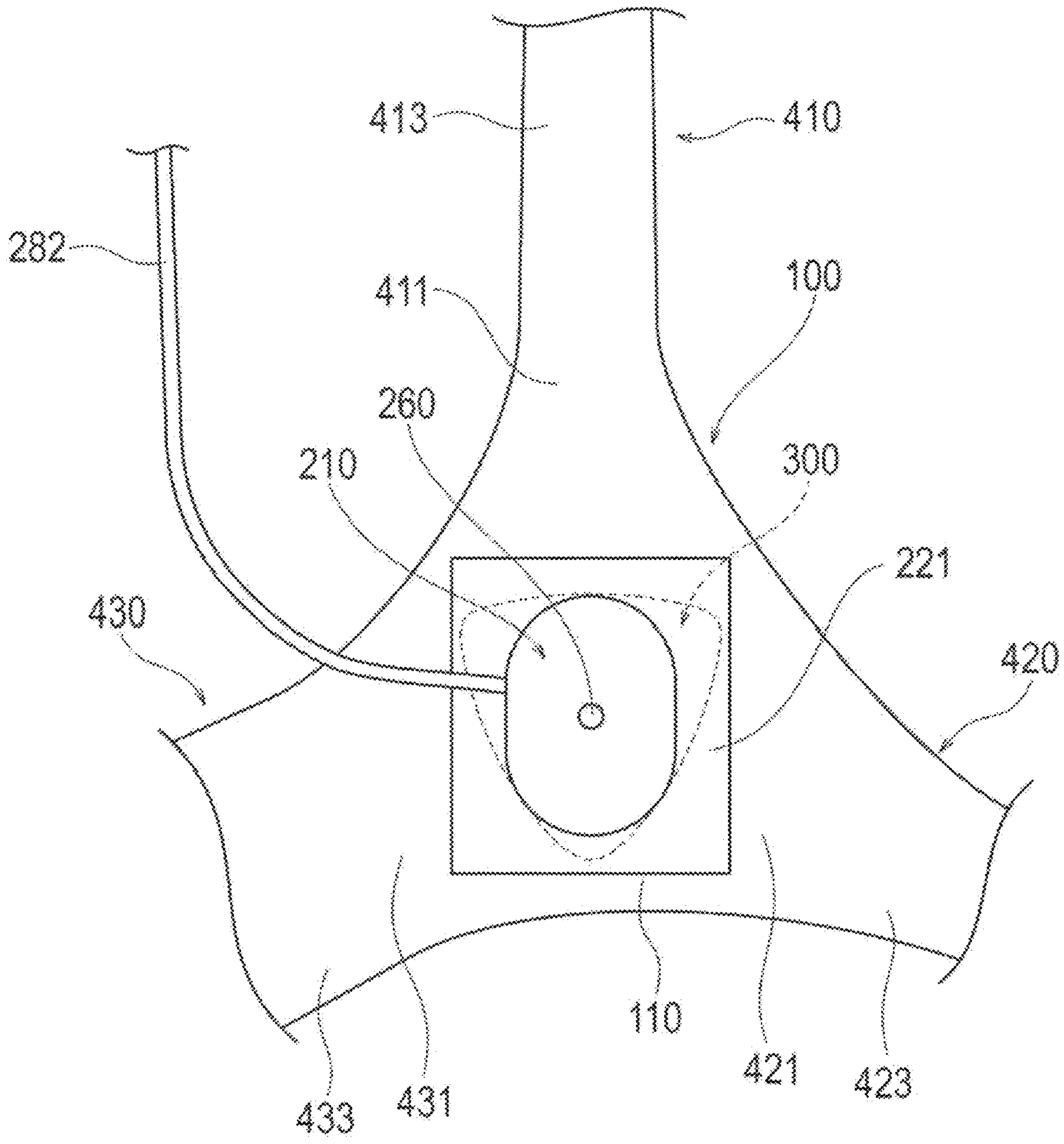
FIG. 4 is an enlarged view of part of the hemostatic device seen from an inner surface side of the cover member.

As illustrated in FIGS. 1 and 2, the injection portion 270 includes a connector incorporating a check valve (not illustrated). A syringe (not illustrated) may be connected to the injection portion 270.

A buffer member 281 having an inflatable space is disposed between the injection portion 270 and the inflatable portion 210. The buffer member 281 is formed of a flexible bag-shaped member in which a space is formed. The buffer member 281 may be provided with an arrow-shaped marker indicating an insertion direction of the syringe into the injection portion 270.

The injection portion 270 is connected to one end side of the buffer member 281. A lumen of the injection portion 270 communicates with the space of the buffer member 281. However, while the check valve incorporated in the injection portion 270 is closed, communication between the lumen of the injection portion 270 and the space of the buffer member 281 is blocked.

A tube 282 having flexibility (flexible tube) is connected to the other end side of the buffer member 281. The lumen of the tube 282 communicates with the space of the buffer member 281. In the tube 282, the other end portion opposite to the one end portion connected to the buffer member 281 is connected to the inflatable portion 210. The lumen of the tube 282 communicates with the lumen 210*a* of the inflatable portion 210.

To inflate the inflatable portion 210, the operator inserts a distal tubular portion of a syringe (not illustrated) into the injection portion 270 and opens the check valve. The operator injects air in the syringe into the lumen 210*a* of the inflatable portion 210 by pushing a pusher of the syringe in a state where the check valve of the injection portion 270 is opened.

When air is injected into the lumen 210*a* of the inflatable portion 210, the inflatable portion 210 inflates. When the inflatable portion 210 inflates, the buffer member 281 communicating with the lumen 210*a* of the inflatable portion 210 via the tube 282 inflates. By visually confirming the inflating of the buffer member 281, the operator can easily grasp that the inflatable portion 210 inflates without leakage of air.

When deflating the inflatable portion 210, the operator inserts the distal tubular portion of the syringe into the injection portion 270 and pulls the pusher of the syringe. The operator can discharge the air in the lumen 210*a* of the inflatable portion 210 to the syringe by performing the above operation.

The injection portion 270, the buffer member 281, and the tube 282 may be prepared and provided in a state of being connected to the inflatable portion 210 or may be prepared and provided in a state of being separated from the inflatable portion 210. In addition, the injection portion 270 is not particularly limited as to a specific configuration, and the like, as long as the injection portion 270 can operate supply of the fluid to the lumen 210*a* of the inflatable portion 210 and discharge of the fluid from the lumen 210*a* of the inflatable portion 210.

<Support Member>

As illustrated in FIGS. 5, 6, 7, 8, and 9, the support member 300 includes an upper end portion 301 disposed on a distal side of the inflatable portion 210, a lower end portion 302 disposed on a proximal side of the inflatable portion 210, and a pair of side surface portions 303 and 304 connecting the upper end portion 301 and the lower end portion 302.

The distal side of the inflatable portion 210 means an end portion side (the upper side of FIGS. 5 and 25, the side on which the curved portion 224*a* is located) disposed on the fingertip side (distal side) of the patient in the inflatable portion 210 when the hemostatic device 10 is attached to the right hand H1 of the patient. In addition, the proximal side of the inflatable portion 210 means an end portion side (the lower side of FIGS. 5 and 25, the side on which the curved portion 224*b* is located) disposed on the forearm Ar side of the patient in the inflatable portion 210 when the hemostatic device 10 is attached to the right hand H1 of the patient.

Figure 8:
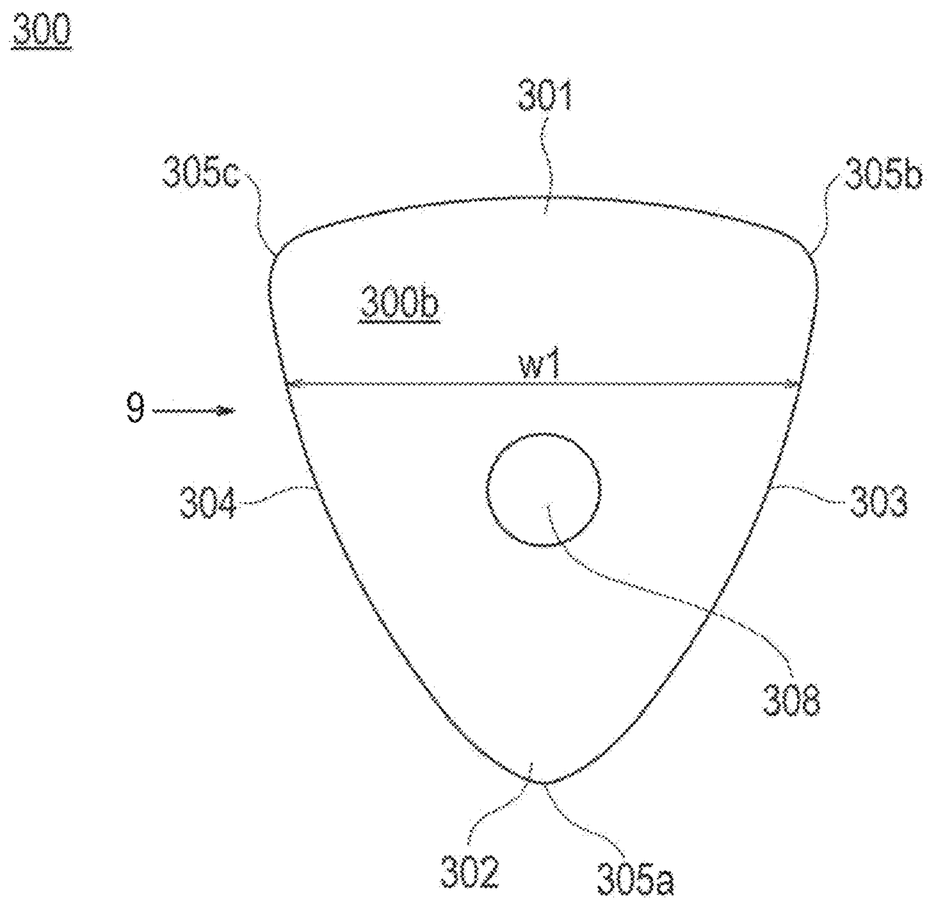
FIG. 8 is a plan view of the support member.

As illustrated in FIG. 8, the support member 300 is configured such that a width w1 of the support member 300 decreases from the upper end portion 301 toward the lower end portion 302.

Figure 9:
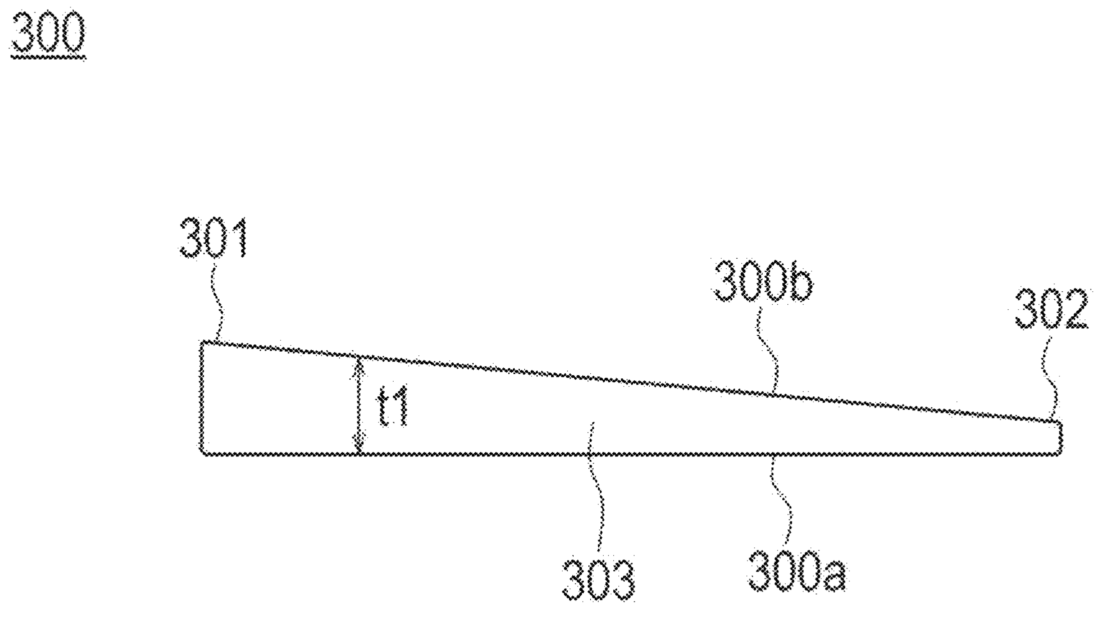
FIG. 9 is a side view of the support member seen from a direction of an arrow 9 in FIG. 8.

As illustrated in FIG. 9, the support member 300 is configured such that a thickness t1 of each of the side surface portions 303 and 304 decreases from the upper end portion 301 toward the lower end portion 302. In other words, the upper surface 300*b* of the support member 300 is inclined toward the lower surface 300*a* from the upper end portion 301 toward the lower end portion 302 in the cross-sectional view illustrated in FIG. 6 and the side view illustrated in FIG. 9.

As illustrated in FIG. 6, the lower surface 300*a* is a surface on a side where the inflatable portion 210 is disposed, and the upper surface 300*b* is a surface on a side where the main body portion 110 of the cover member 100 is disposed.

As illustrated in FIG. 5, the support member 300 has a bilaterally symmetrical shape with respect to the long axis C (axis along the extending direction) of the first band body portion 410. Specifically, as illustrated in FIG. 8, the support member 300 has a substantially triangular planar shape.

Each of corner portions 305*a*, 305*b*, and 305*c* located on the outer peripheral side surface of the support member 300 has a rounded shape.

Figure 7:
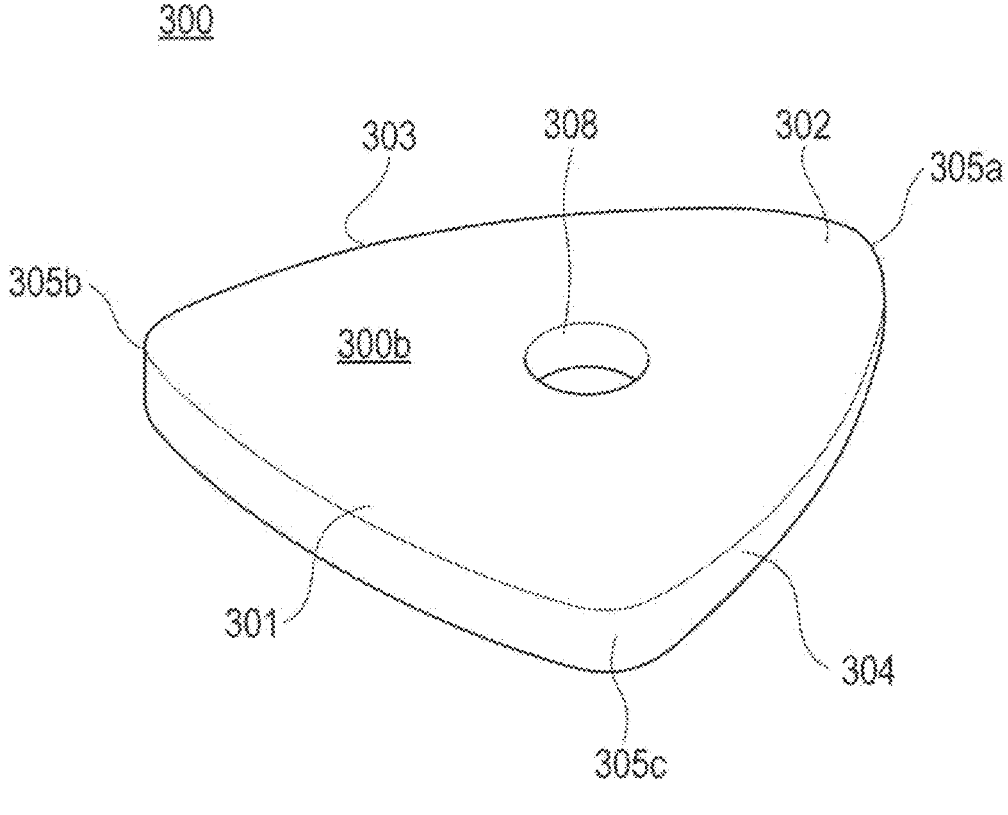
FIG. 7 is a perspective view of a support member.

As illustrated in FIG. 7, the support member 300 has a hole portion 308 penetrating the support member 300 in a thickness direction. As illustrated in FIG. 6, the hole portion 308 can be disposed at a position overlapping the inflatable portion 210. In the present embodiment, the hole portion 308 is disposed at a position overlapping the marker portion 260 (see FIG. 10) located on the top surface portion 241. The illustration of the hole portion 308 is omitted in some drawings.

Figure 25:
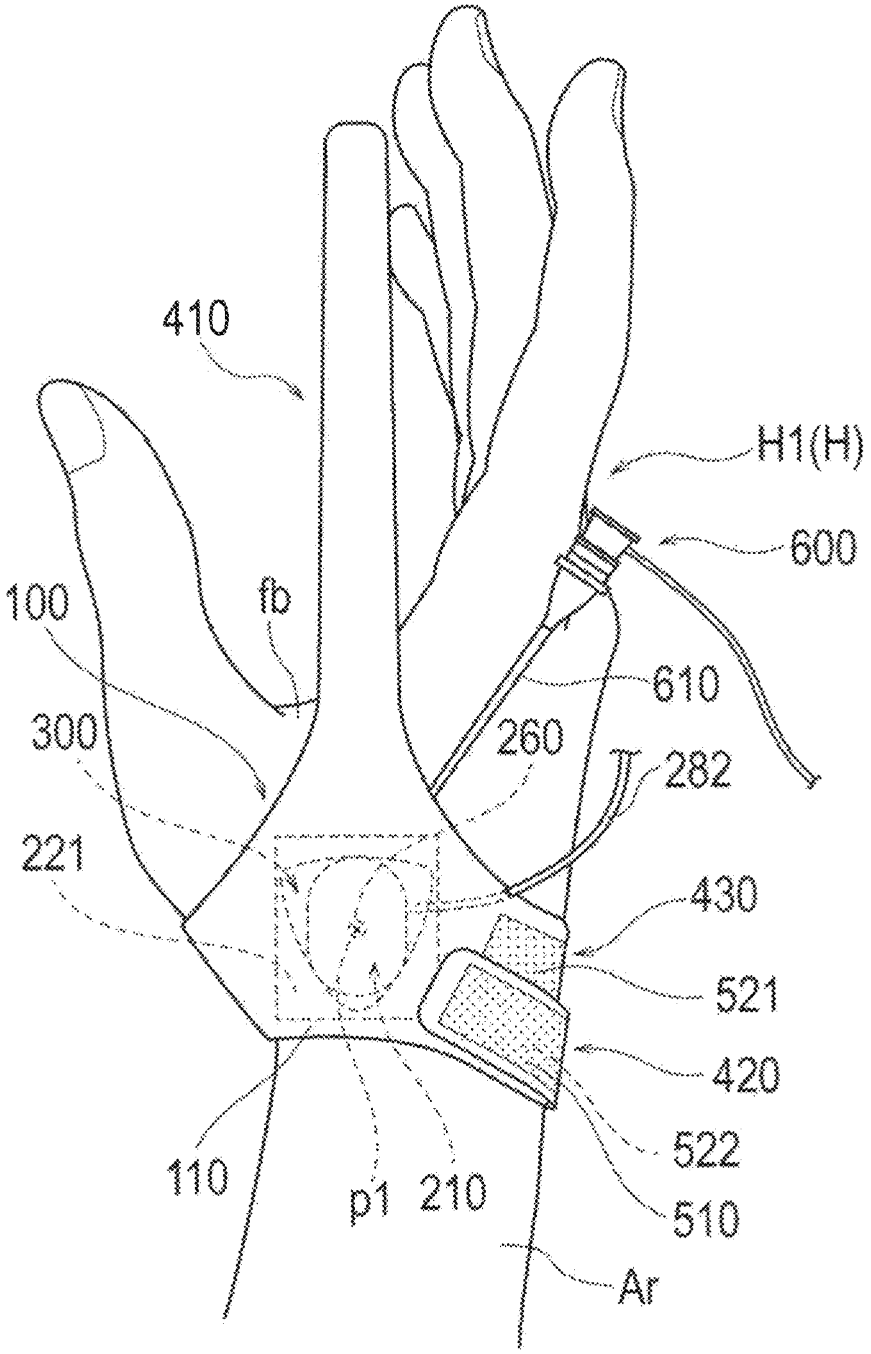
FIG. 25 is a view schematically illustrating a use example of the hemostatic device.

In the hemostatic device 10, a portion of the sheet member 211 where the marker portion 260 is provided, a portion of the connection member 221 overlapping the marker portion 260, and a portion of the main body portion 110 of the cover member 100 overlapping the marker portion 260 can be formed to be transparent. In a case where the respective members 100, 211, and 221 are configured in this manner, as illustrated in FIGS. 24 to 26, when attaching the hemostatic device 10 to the right hand H1 of the patient, the operator can easily visually confirm the position of the marker portion 260 disposed on the top surface portion 241 of the inflatable portion 210 and/or the first puncture site p1 via the hole portion 308 of the support member 300 and the transparent portions of the members 100, 211, and 221. In a case where a portion of the support member 300 overlapping the marker portion 260 is formed to be transparent in the support member 300, the hole portion 308 does not have to be provided. The term "transparent" includes colored transparent, colorless transparent, and translucent.

The support member 300 can be formed of a member having rigidity higher than that of the inflatable portion 210. With such a configuration, the support member 300 can press the inflatable portion 210 against the right hand H1 of the patient when the inflatable portion 210 applies a compressive force to the first puncture site p1 as illustrated in FIG. 27. This makes it possible to prevent the inflatable portion 210 from floating (lifting-off or separating) from the right hand H1 of the patient.

In a case where the inflatable portion 210 (the sheet member 211 and the connection member 221) is formed of each of the above-described materials, as a constituent material from which the support member 300 may be fabricated, for example, acrylic resin, polyvinyl chloride (particularly hard polyvinyl chloride), polyolefin such as polyethylene, polypropylene, or polybutadiene, polystyrene, poly-(4-methylpentene-1), polycarbonate, ABS resin, polymethyl methacrylate (PMMA), polyacetal, polyacrylate, polyacrylonitrile, polyvinylidene fluoride, ionomer, acrylonitrile-butadiene-styrene copolymer, polyethylene terephthalate (PET), or the like, can be used.

<Cover Member>

As illustrated in FIGS. 1, 2, 3, and 4, the cover member 100 includes the main body portion 110, the first band body portion 410, the second band body portion 420, and the third band body portion 430.

Each of the band body portions 410, 420, and 430 extends from the main body portion 110. As illustrated in FIGS. 5 and 6, the inflatable portion 210 and the support member 300 are disposed in the main body portion 110. That is, the main body portion 110, the inflatable portion 210 and the support member 300 are positioned in overlying relation to one another.

Each of the band body portions 410, 420, and 430 may be integrally configured with the main body portion 110, or members forming the respective band body portions 410, 420, and 430 may be connected to the main body portion 110.

The first band body portion 410 is configured to be disposed between the fingers of the patient. The first band body portion 410 extends in a predetermined first direction.

As illustrated in FIGS. 1 and 2, the first band body portion 410 includes one end portion 411 located on the main body portion 110 side of the cover member 100, the other end portion 412 located on the opposite side of the one end portion 411, and a main body portion 413 extending between the one end portion 411 and the other end portion 412.

For example, as illustrated in FIG. 26, the first band body portion 410 can be disposed so as to be hooked on the inter-finger portion fb located between the thumb and the index finger of the right hand H1 of the patient in a state where the inflatable portion 210 is disposed at the first puncture site p1.

The second band body portion 420 extends in a second direction different from the first direction which is the extending direction of the first band body portion 410.

As illustrated in FIGS. 1 and 2, the second band body portion 420 includes one end portion 421 located on the main body portion 110 side of the cover member 100, the other end portion 422 located on the opposite side of the one end portion 421, and a main body portion 423 extending between the one end portion 421 and the other end portion 422.

The third band body portion 430 extends in a third direction different from each of the first direction which is the extending direction of the first band body portion 410 and the second direction which is the extending direction of the second band body portion 420.

As illustrated in FIGS. 1 and 2, the third band body portion 430 includes one end portion 431 located on the main body portion 110 side of the cover member 100, the other end portion 432 located on the opposite side of the one end portion 431, and a main body portion 433 extending between the one end portion 431 and the other end portion 432.

As illustrated in FIGS. 25 and 26, the second band body portion 420 and the third band body portion 430 can be disposed so as to be wound along the outer periphery of the right hand H1 when the hemostatic device 10 is attached to the right hand H1 of the patient.

The constituent material from which each of the band body portions 410, 420, and 430 may be fabricated is not particularly limited and can be, for example, a vinyl chloride resin, a polyurethane resin, a polyester resin, or the like. Further, a shape, a length, a thickness, and the like, of each of the band body portions 410, 420, and 430 are not particularly limited.

Four securing sites, that is, a first securing site 510, a second securing site 520, a third securing site 530, and a fourth securing site 540 capable of securing the cover member 100 to the right hand H1 are disposed in the band body portions 410, 420, and 430.

As illustrated in FIG. 1, the first securing site 510 is disposed on an outer surface of the main body portion 423 of the second band body portion 420.

As illustrated in FIG. 1, the second securing site 520 is disposed on an outer surface of the main body portion 433 of the third band body portion 430. In the second securing site 520, an end portion located on the other end portion 432 side of the third band body portion 430 branches into a first branch portion 521 and a second branch portion 522.

As illustrated in FIG. 2, the third securing site 530 is disposed on an inner surface of the main body portion 423 of the second band body portion 420.

As illustrated in FIG. 2, the fourth securing site 540 is disposed on an inner surface of the main body portion 413 of the first band body portion 410.

The first securing site 510 and the second securing site 520 are formed as a male side of a hook-and-loop fastener. The third securing site 530 and the fourth securing site 540 are formed as a female side of the hook-and-loop fastener. The hook-and-loop fastener in the present specification is a hook-and-loop fastener, and is, for example, Magic Tape (registered trademark) or Velcro (registered trademark).

<Use Example of Hemostatic Device>

Next, a use example of the hemostatic device 10 will be described with reference to FIGS. 23 to 27.

In the present use example, a procedure that may be employed using the hemostatic device 10 to stop bleeding at the first puncture site p1 formed on the right hand H1 of the patient illustrated in FIG. 23 will be described.

FIG. 24 illustrates a state after various procedures performed using the sheath tube 610 of the introducer 600 inserted into the first puncture site p1 are completed.

When attaching the hemostatic device 10 to the right hand H1, the operator disposes the inflatable portion 210 so as to overlap the first puncture site p1 as illustrated in FIG. 24. In this event, the operator disposes the marker portion 260 at the first puncture site p1 while visually confirming the marker portion 260 located on the top surface portion 241 of the inflatable portion 210 through the hole portion 308 (see FIG. 7) formed in the support member 300. By performing such operation, the operator can appropriately position the inflatable portion 210 and the support member 300 at the first puncture site p1.

In addition, even in a state where the inflatable portion 210 is deflated after the inflatable portion 210 has been inflated once as described above, the position of the marker portion 260 in the plane direction of the top surface portion 241 is substantially the same position in the initial shape, so that the operator can appropriately align the inflatable portion 210 with the first puncture site p1 based on the marker portion 260.

When attaching the hemostatic device 10 to the right hand H1, the operator disposes the hemostatic device 10 such that the support member 300 overlaps the metacarpal B1 of the index finger and the metacarpal B2 of the thumb. As illustrated in FIG. 23, an interval between the metacarpal B1 of the index finger and the metacarpal B2 of the thumb gradually narrows from the fingertip side toward the forearm Ar side. As described above, the width w1 of the support member 300 decreases from the upper end portion 301 side toward the lower end portion 302 side (see FIG. 8). Thus, the operator can dispose the support member 300 along the metacarpal B1 of the index finger and the metacarpal B2 of the thumb. The operator can prevent a gap from being formed between the inflatable portion 210 and the right hand H1 by disposing the support member 300 along the metacarpal B1 of the index finger and the metacarpal B2 of the thumb.

As illustrated in FIG. 25, the operator wraps the second band body portion 420 and the third band body portion 430 along the outer periphery of the right hand H1. The operator can connect the second band body portion 420 and the third band body portion 430 via the securing sites 520 and 530 by bringing the third securing site 530 (see FIG. 2) disposed on the inner surface of the second band body portion 420 into contact with the second securing site 520 (see FIG. 1) disposed on the outer surface of the third band body portion 430. The operator can firmly wrap each of the band body portions 420 and 430 along the outer periphery of the right hand H1 by connecting the band body portions 420 and 430 in a state where the support member 300 overlaps the metacarpal B1 of the index finger and the metacarpal B2 of the thumb.

In addition, when stopping bleeding at the first puncture site p1, the operator can connect the third securing site 530 disposed on the inner surface of the second band body portion 420 to the second branch portion 522 of the second securing site 520. The first puncture site p1 is located closer to the fingertip of the right hand H1 of the patient than the second puncture site p2 (see FIG. 10). Thus, when stopping bleeding at the first puncture site p1, the operator connects the second band body portion 420 and the third band body portion 430 via the second branch portion 522 located closer to the forearm Ar of the right hand H1 of the patient than the first branch portion 521, whereby a range in which each of the band body portions 420 and 430 restrains the right hand H1 of the patient can be narrowed.

As illustrated in FIG. 26, the operator disposes part of the first band body portion 410 on the palm side of the right hand H1 of the patient while putting the first band body portion 410 through the inter-finger portion fb. In this event, the operator brings the fourth securing site 540 (see FIG. 2) disposed on the inner surface of the first band body portion 410 into contact with the first securing site 510 (see FIG. 1) disposed on the outer surface of the second band body portion 420, thereby connecting the first band body portion 410 and the second band body portion 420 via the respective securing sites 510 and 540.

The support member 300 has a substantially triangular shape having three sides (see FIG. 8). The hemostatic device 10 has three band body portions 410, 420, and 430 disposed to extend from the respective sides of the support member 300. Thus, the hemostatic device 10 can secure the cover member 100 to the right hand H1 in a state where an equal force is applied to the respective sides of the support member 300 by connecting the band body portions 410, 420, and 420 to each other.

The support member 300 has a bilaterally symmetrical shape with respect to the long axis C (see FIG. 5) of the first band body portion 410. Thus, the hemostatic device 10 can apply an equal force along a bilaterally symmetrical direction with respect to the support member 300 by wrapping the band body portions 420 and 430 extending bilaterally symmetrically based on the first band body portion 410 around the right hand H1. As a result, in the hemostatic device 10, it is possible to prevent the support member 300 from being displaced in a state where the support member 300 is disposed on the right hand H1.

The operator connects the syringe to the injection portion 270 in a state where the hemostatic device 10 is attached to the right hand H1. The operator operates the syringe to inflate the inflatable portion 210 by injecting air into the inflatable portion 210. As illustrated in FIG. 26, in the hemostatic device 10, when the inflatable portion 210 inflates, the inflatable portion 210 applies a compressive force to the first puncture site p1.

When the inflatable portion 210 inflates in a state where the hemostatic device 10 is attached to the right hand H1, the support member 300 presses the inflatable portion 210 against the right hand H1 of the patient. Thereby, in the hemostatic device 10, it is possible to prevent the inflatable portion 210 from floating (lifting-off or separating) from the right hand H1 of the patient.

When stopping bleeding using the hemostatic device 10, the operator can more strongly tighten the first band body portion 410 disposed in the inter-finger portion fb in order to increase the securing force of the support member 300 with respect to the right hand H1. By tightening the first band body portion 410 as described above, the operator can firmly secure the support member 300 to the right hand H1 even in a case where the support member 300 is disposed in an unstable state on the right hand H1 of the patient. However, if the first band body portion 410 is strongly tightened as described above, the patient may feel pain. In addition, if the hemostatic device 10 is secured to the right hand H1 so as to avoid strongly tightening the first band body portion 410, the lower surface 300*a* of the support member 300 may be disposed while tilting with respect to the body surface of the right hand H1.

In order to solve the above problem, the hemostatic device 10 is configured such that the thickness of each of the side surface portions 303 and 304 of the support member 300 decreases from the upper end portion 301 toward the lower end portion 302. In addition, the first band body portion 410 configured to be disposed in the inter-finger portion fb extends from the upper end portion 301 side of the support member 300 and is configured to press the upper end portion 301 side of the support member 300 against the right hand H1. Thus, when the inflatable portion 210 starts inflating in a state where the hemostatic device 10 is attached to the right hand H1, the inflatable portion 210 applies a force to the upper end portion 301 of the support member 300. The upper end portion 301 side of the support member 300 floats (lifts-off) by the force applied by the inflatable portion 210. Accordingly, as illustrated in FIG. 27, the support member 300 is disposed such that the lower surface 300*a* of the support member 300 is substantially parallel to the body surface of the right hand H1.

Thus, the hemostatic device 10 can apply a compressive force in a direction perpendicular to the first puncture site p1 when the inflatable portion 210 inflates.

The support member 300 has a shape in which each of the corner portions 305*a*, 305*b*, and 305*c* is rounded (see FIG. 8). Thus, in the hemostatic device 10, it is possible to prevent each of the corner portions 305*a*, 305*b*, and 305*c* of the support member 300 from biting into the right hand H1 when the inflatable portion 210 inflates and applies the compressive force to the first puncture site p1.

According to the above procedure, the operator can stop bleeding at the first puncture site p1 formed on the right hand H1 using the hemostatic device 10.

When stopping bleeding at the second puncture site p2 (see FIG. 23) using the hemostatic device 10, the operator can connect the third securing site 530 (see FIG. 2) disposed on the inner surface of the second band body portion 420 to the first branch portion 521 (see FIG. 1) of the second securing site 520 disposed on the outer surface of the third band body portion 430. When stopping bleeding at the second puncture site p2, the operator connects the second band body portion 420 and the third band body portion 430 using the first branch portion 521 located closer to the fingertip of the patient than the second branch portion 522, so that a range in which each of the band body portions 410 and 420 restrains the right hand H1 can be narrowed.

As described above, the hemostatic device 10 according to the present embodiment includes the cover member 100 configured to cover the first puncture site p1, and the pressing member 200 connected to the cover member 100 and configured to compress the first puncture site p1. The pressing member 200 includes the inflatable portion 210 configured to be able to inflate and deflate by injection of a fluid, and the injection portion 270 configured to be able to inject a fluid into the inflatable portion 210. In the inflated state, the inflatable portion 210 includes the bottom surface portion 220, the column portion 230 rising from the bottom surface portion 220, and the curved surface portion 240 forming the upper surface of the column portion 230. The thickness D2 of the curved surface portion 240 is formed to be thinner than the thickness D1 of the column portion 230.

According to the hemostatic device 10 configured as described above, the inflatable portion 210 has high restorability such that the inflatable portion 210 deforms to substantially the same shape as the initial shape when the inflatable portion 210 in the inflated state is deflated. Thereby, in the hemostatic device 10, an arbitrary portion (for example, the top surface portion 241 on which the marker portion 260 is located) of the inflatable portion 210 can be easily aligned with the first puncture site p1, for example, when the inflatable portion 210 is aligned with the first puncture site p1 again after the inflatable portion 210 disposed at the first puncture site p1 in the inflated state is deflated. Accordingly, when deflating the inflatable portion 210 in order to change the arrangement of the inflatable portion 210 with respect to the first puncture site p1, the operator does not need to perform operation such as pressing the outer surface of the inflatable portion 210 with the fingers. Thus, in the hemostatic device 10, when the inflatable portion 210 is aligned with the first puncture site p1 again, it is possible to prevent blood flowing from the first puncture site p1 from unnecessarily adhering to the outer surface of the inflatable portion 210 or prevent contamination at the first puncture site p1.

In addition, in the hemostatic device 10, the inflatable portion 210 includes the marker portion 260 for aligning the inflatable portion 210 with the first puncture site p1. The curved surface portion 240 includes the top surface portion 241 on which the marker portion 260 is located, and the inclined portion 243 located around the top surface portion 241 and connected to the column portion 230. The inclined portion 243 has the thin portion 253 that surrounds the top surface portion 241 and is formed to be thinner than the thickness D1' of the top surface portion 241.

According to the hemostatic device 10 configured as described above, in the initial stage where deflating of the inflatable portion 210 is started, deformation is started such that the thin portion 253 is bent toward the bottom surface portion 220, and the top surface portion 241 having a larger thickness than the thin portion 253 moves so as to approach the bottom surface portion 220 while preventing the surface shape from being greatly impaired due to the deformation of the thin portion 253. It is therefore possible to prevent the marker portion 260 located on the top surface portion 241 from being displaced in a plane direction of the top surface portion 241 when the inflatable portion 210 deflates.

In addition, the top surface portion 241 is thicker than the thin portion 253, so that it is possible to prevent the top surface portion 241 from being excessively crushed when the top surface portion 241 applies a compressive force to the first puncture site p1 in a state where the inflatable portion 210 is inflated. Thus, the hemostatic device 10 can effectively apply the compressive force from the top surface portion 241 to the first puncture site p1.

The thin portion or thinned portion 253 is disposed so as to surround the entire circumference of the top surface portion 241.

According to the hemostatic device 10 configured as described above, when the inflatable portion 210 starts to deflate, the thin portion 253 surrounding the entire circumference of the top surface portion 241 serves as a starting point of deformation. The inflatable portion 210 deflates in a state where the entire circumference of the top surface portion 241 is surrounded by the thin portion 253, so that it is possible to prevent the surface shape of the top surface portion 241 located closer to the centers C1 and C2 than the thin portion 253 at the time of deflating from being impaired. It is therefore possible to prevent the marker portion 260 located on the top surface portion 241 from being displaced in the plane direction of the top surface portion 241 when the inflatable portion 210 deflates.

The thin portion or thinned portion 253 is located at a position that is point symmetrical about the marker portion 260.

According to the hemostatic device 10 configured as described above, the inflatable portion 210 can maintain a relative positional relationship between the marker portion 260 and the thin portion 253 without being affected by the attachment position and direction of the inflatable portion 210 with respect to the right hand H1. Accordingly, in the hemostatic device 10, even when the inflatable portion 210 in a state where inflating and deflating have been repeated is aligned with the first puncture site p1 again, the relative positional relationship between the marker portion 260 and the thin portion 253 is suitably maintained, so that the marker portion 260 can be appropriately aligned with the first puncture site p1.

The inflatable portion 210 forms the first height h1 between the bottom surface portion 220 and the top surface portion 241 in a state where the inflatable portion 210 is inflated. The thin portion 253 is located closer to the top surface portion 241 than the intermediate position 215 of the first height h1.

According to the hemostatic device 10 configured as described above, the thin portion 253 of the inflatable portion 210 is located closer to the top surface portion 241 than the intermediate position 215, so that when the inflatable portion 210 starts inflating, the thin portion 253 serves as a starting point of the inflating, and the inflating on the top surface portion 241 side progresses more quickly than the inflating on the column portion 230 side. Thus, when the inflatable portion 210 inflates, the inflatable portion 210 can prevent the inflating from progressing on the column portion 230 side. If the column portion 230 inflates and the column portion 230 inflates in the lateral direction, the first height h1 corresponding to the maximum inflating height when the inflatable portion 210 inflates decreases. As a result, a compressive force to be applied to the first puncture site p1 by the inflatable portion 210 decreases. In the hemostatic device 10, it is possible to prevent decrease of the compressive force as described above.

The inflatable portion 210 forms the recess 217 and the protrusion 218 surrounding the recess 217 in a state where the inflatable portion 210 is deflated. The protrusion 218 is formed by the column portion 230, and the top surface portion 241 is located in the recess 217.

According to the hemostatic device 10 configured as described above, the top surface portion 241 where the marker portion 260 is located is disposed in the recess 217 in a state where the inflatable portion 210 is deflated. The protrusion 218 surrounding the recess 217 applies tension so as to pull the recess 217 to the circumference. This makes wrinkles and twists less likely to occur in the recess 217. In the hemostatic device 10, when the inflatable portion 210 is disposed on the right hand H1, the marker portion 260 is disposed along the surface of the top surface portion 241 with less wrinkles and twists. Thus, in the hemostatic device 10, the marker portion 260 can be easily aligned with the first puncture site p1. In addition, in the hemostatic device 10, it is possible to prevent decrease in visibility of the marker portion 260 located in the recess 217 and visibility of the first puncture site p1 that is to be confirmed through the recess 217 as a result of wrinkles and twists being less likely to occur in the recess 217. Thus, in the hemostatic device 10, the marker portion 260 can be more easily aligned with the first puncture site p1.

The height h2 of the protrusion 218 is shorter (less) than the distance L1 from the top of the protrusion 218 to the center of the bottom surface portion 220 in the plane direction.

In the hemostatic device 10 configured as described above, the height h2 of the protrusion 218 is shorter (less) than the distance L1, and thus, even if the protrusion 218 falls down toward the recess 217 as a result of the protrusion 218 coming into contact with the body surface of the right hand H1, or the like, when the inflatable portion 210 in the deflated state is attached to the right hand H1, it is possible to prevent the protrusion 218 from overlapping the center of the bottom surface portion 220. This makes it possible for the operator to appropriately dispose the center of the top surface portion 241 at the first puncture site p1. In the hemostatic device 10, the marker portion 260 is disposed at the center of the top surface portion 241, so that it is possible to prevent the protrusion 218 from overlapping the marker portion 260 even when the protrusion 218 falls down toward the recess 217 side. This makes it possible for the operator to appropriately dispose the marker portion 260 at the first puncture site p1.

The bottom surface portion 220 includes two straight portions 223*a* and 223*b* facing each other across the marker portion 260, and two curved portions 224*a* and 224*b* facing each other across the marker portion 260 and connecting the two straight portions 223*a* and 223*b*.

In the hemostatic device 10 configured as described above, when the inflatable portion 210 inflates, the column portion 230 forming the inflatable portion 210 rises from the bottom surface portion 220 in a shape similar to the bottom surface portion 220 (shape in which both overlap in plan view). Thus, the inflatable portion 210 of the hemostatic device 10 has a predetermined region extending in the lateral direction between the two straight portions 223*a* and 223*b* connected by the two curved portions 224*a* and 224*b*. Thus, in the hemostatic device 10, when the inflatable portion 210 applies a compressive force to the first puncture site p1, the area of the inflatable portion 210 (the area of the top surface portion 241) can be secured to be equal to or larger than a predetermined size. This makes it possible for the inflatable portion 210 to firmly apply a compressive force to the first puncture site p1. In addition, in the inflatable portion 210, the area of the inflatable portion 210 is secured to a predetermined size, and thus, even when the inflatable portion 210 is displaced from the first puncture site p1, the compressive force is less likely to decrease due to influence of displacement of the inflatable portion 210. As a result, even if the inflatable portion 210 is slightly displaced from the first puncture site p1, the compressive force can be appropriately applied.

The bottom surface portion 220 has the long axis A1 passing through the center C in the lateral direction of the bottom surface portion 220 and the short axis A2 passing through the center C2 in the longitudinal direction of the bottom surface portion 220 and shorter than the long axis A1 in the inflated state of inflatable portion 210. The thickness of the inflatable portion 210 is bilaterally symmetrical with respect to the long axis A1.

In the hemostatic device 10 configured as described above, the thickness of the inflatable portion 210 is bilaterally symmetrical with respect to the long axis A1. The inflatable portion 210 can inflate bilaterally symmetrically with respect to the long axis A1, and thus, a difference in an inflating amount hardly occurs at a position in the horizontal direction with respect to the long axis A1. Accordingly, the inflatable portion 210 can apply a compressive force along a direction substantially perpendicular to the first puncture site p1. Furthermore, the inflatable portion 210 can inflate bilaterally symmetrically with respect to the long axis A1, so that the inflatable portion 210 is less likely to be displaced from the first puncture site p1 in the inflated state.

In addition, the thickness of the inflatable portion 210 is bilaterally symmetrical with respect to the long axis A1, and thus, when the inflatable portion 210 deflates, the inflatable portion 210 deflates uniformly in the horizontal direction with reference to the long axis A1. Thus, when the inflatable portion 210 deflates, a relative positional relationship between the bottom surface portion 220 and the top surface portion 241 can be maintained. In particular, in the present embodiment, the marker portion 260 is located on the top surface portion 241, so that it is possible to prevent the marker portion 260 from being displaced in the plane direction due to deflating of the inflatable portion 210.

Although the hemostatic device has been described above through the embodiment, the present invention is not limited only to the content described in the specification, and can be appropriately changed based on the description of the claims.

The shape, dimensions, and the like, of each portion of the hemostatic device are not particularly limited as long as hemostatic compression can be performed on the puncture site by the inflatable portion disposed at the puncture site, and can be appropriately changed.

The specific shape (planar shape or cross-sectional shape) of the inflatable portion is not limited to the shape illustrated in the embodiment.

The hemostatic device can also be configured for the purpose of hemostasis other than the puncture site formed on the hand. For example, the hemostatic device can also be applied to hemostasis of a puncture site formed on an arm, a leg, or the like, of a patient using the inflatable portion of the embodiment.

The hemostatic device does not have to include a support member. In addition, even in a case where the hemostatic device includes a support member, the shape and the structure of the support member are not limited to the configuration described in the embodiment.

The shape and the structure of the cover member included in the hemostatic device are also not particularly limited. In addition, in a case where the hemostatic device is configured to include the band body portion, the specific shape and the structure of the band body portion are not particularly limited.

The detailed description above describes embodiments of a hemostatic device and method of use representing examples of the hemostatic device and method of use disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents that fall within the scope of the claims are embraced by the claims.

REFERENCE SIGNS LIST

10 Hemostatic device
100 Cover member
110 Main body portion of cover member
200 Pressing member
210 Inflatable portion
210*a* Lumen of inflatable portion 211 Sheet member
211*a* Edge portion of sheet member
215 Intermediate position
217 Recess
218 Protrusion
220 Bottom surface portion
221 Connection member
223*a* Straight portion
223*b* Straight portion
224*a* Curved portion
224*b* Curved portion
230 Column portion
231 Root portion of column portion
240 Curved surface portion
241 Top surface portion
243 Inclined portion
253 Thin portion
260 Marker portion
270 Injection portion
281 Buffer member
282 Tube
300 Support member
410 First band body portion
420 Second band body portion
430 Third band body portion
510 First securing site
520 Second securing site
530 Third securing site
540 Fourth securing site
600 Introducer
A1 Long axis of bottom surface portion
A2 Short axis of bottom surface portion
C1 Center in lateral direction of bottom surface portion
C2 Center in longitudinal direction of bottom surface portion
D1 Thickness of curved surface portion
D1' Thickness of top surface portion
D2 Thickness of column portion
D3 Thickness of thin portion
h1 First height
h2 Height of protrusion
L1 Distance from top of protrusion to center of bottom surface portion in plane direction
H Hand
H1 Right hand
Ar Forearm
B1 Metacarpal of index finger
B2 Metacarpals of Thumb
T1 Extensor pollicis longus tendon
T2 Extensor pollicis brevis tendon
V1 Blood vessel (distal radial artery)
V2 Arteries located at snuff box
p1 First puncture site (puncture site)
p2 Second puncture site (puncture site)
fb Inter-finger portion

What is claimed is:

1. A hemostatic device comprising:
a cover member configured to cover a puncture site on a patient;
a pressing member connected to the cover member and configured to compress the puncture site;
the pressing member comprising: an inflatable portion configured to be inflated to an inflated state by introducing a fluid into an interior of the inflatable portion and to be deflated; and an injection portion in communication with the interior of the inflatable portion and configured to inject the fluid into the interior of the inflatable portion;
the inflatable portion including a bottom surface portion, a column portion extending away from the bottom surface portion, a curved surface portion forming an upper surface of the column portion in the inflated state of the inflatable portion, and a marker for aligning the inflatable portion with the puncture site;
a thickness of the curved surface portion is thinner than a thickness of the column portion;
the curved surface portion includes a top surface portion on which the marker is located and an inclined portion that surrounds the top surface portion and is connected to the column portion; and
the inclined portion includes a thinned portion that surrounds the top surface portion and has a thickness less than a thickness of the top surface portion.

2. The hemostatic device according to claim 1, wherein the thinned portion that has the thickness less than the top surface portion surrounds an entire circumference of the top surface portion.

3. The hemostatic device according to claim 1, wherein the thinned portion is located at a position that is point symmetrical about the marker.

4. The hemostatic device according to claim 1, wherein
the inflatable portion has a first height between the bottom surface portion and the top surface portion in the inflated state in which the inflatable portion is inflated, and
the thinned portion is located closer to the top surface portion than an intermediate position of the first height.

5. The hemostatic device according to claim 1, wherein
the inflatable portion forms a recess and a protrusion surrounding the recess in a deflated state in which the inflatable portion is deflated,
the protrusion is formed by the column portion, and
the top surface portion is located in the recess.

6. The hemostatic device according to claim 5, wherein a height of the protrusion is shorter than a distance from a top portion of the protrusion to a center of the bottom surface portion in a plane direction.

7. The hemostatic device according to claim 1, wherein the bottom surface portion includes two straight portions facing each other across the marker so that the marker is positioned between the two straight portions, and two curved portions connecting the two straight portions and facing each other across the marker so that the marker is positioned between the two curved portions.

8. The hemostatic device according to claim 1, wherein
the bottom surface portion is configured to include a long axis which passes through a center of the bottom surface portion in a lateral direction and a short axis which passes through a center of the bottom surface portion in a longitudinal direction and which is shorter than the long axis in the inflated state in which the inflatable portion is inflated, and
a thickness of the inflatable portion is bilaterally symmetrical with respect to the long axis.

9. A hemostatic device comprising:
a cover member configured to cover a puncture site on a patient;
a pressing member connected to the cover member and configured to compress the puncture site;
the pressing member comprising: an inflatable portion configured to be inflated to an inflated state by introducing a fluid into an interior of the inflatable portion and to be deflated; and an injection portion in communication with the interior of the inflatable portion and configured to inject the fluid into the interior of the inflatable portion;

the inflatable portion including a bottom surface portion, a column portion extending away from the bottom surface portion, and a curved surface portion forming an upper surface of the column portion in the inflated state of the inflatable portion; a thickness of the curved surface portion is thinner than a thickness of the column portion;

the curved surface portion including a top surface portion having a top portion that, in the inflated state of the inflatable portion, is at a position farthest from the bottom surface portion side, the curved surface portion also including an inclined portion that is located around the top surface portion and is connected to the column portion, and the inclined portion including a thinned portion that surrounds the top surface portion and has a thickness less than a thickness of the top surface portion.

10. The hemostatic device according to claim 9, wherein the thinned portion surrounds an entire circumference of the top surface portion.

11. The hemostatic device according to claim 9, wherein the thinned portion is located at a position that is point symmetrical about the top portion of the top surface portion.

12. The hemostatic device according to claim 9, wherein the inflatable portion forms a first height between the bottom surface portion and the top surface portion in the inflated state in which the inflatable portion is inflated, and the thinned portion is located closer to the top surface portion than an intermediate position of the first height.

13. The hemostatic device according to claim 9, wherein the inflatable portion forms a recess and a protrusion surrounding the recess in a state in which the inflatable portion is deflated, the protrusion is formed by the column portion, and the top surface portion is located in the recess.

14. The hemostatic device according to claim 13, wherein a height of the protrusion is less than a distance from a top portion of the protrusion to a center of the bottom surface portion in a plane direction.

15. The hemostatic device according to claim 9, wherein the bottom surface portion is configured to include two straight portions and two curved portions, the two straight portions facing each other across the top surface portion in a plan view of the inflatable portion so that the top surface portion is positioned between the two straight portions in the plan view, and the two curved portions connecting the two straight portions and facing each other across the top surface portion in the plan view so that the top surface portion is positioned between the two curved portions in the plan view.

16. The hemostatic device according to claim 9, wherein the bottom surface portion has a long axis which passes through a center of the bottom surface portion in a lateral direction and a short axis which passes through a center of the bottom surface portion in a longitudinal direction and which is shorter than the long axis in a state where the inflatable portion is inflated, and a thickness of the inflatable portion is bilaterally symmetrical with respect to the long axis.

* * * * *